(12) United States Patent
Biberger

(10) Patent No.: US 10,483,084 B2
(45) Date of Patent: Nov. 19, 2019

(54) OBJECT PREPARATION DEVICE AND PARTICLE BEAM DEVICE HAVING AN OBJECT PREPARATION DEVICE AND METHOD FOR OPERATING THE PARTICLE BEAM DEVICE

(71) Applicant: Carl Zeiss Microscopy GmbH, Jena (DE)

(72) Inventor: Josef Biberger, Wildenberg (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 15/906,039

(22) Filed: Feb. 27, 2018

(65) Prior Publication Data

US 2018/0286632 A1    Oct. 4, 2018

(30) Foreign Application Priority Data

Mar. 4, 2017 (DE) .......... 10 2017 203 553

(51) Int. Cl.
*H01J 37/28* (2006.01)
*H01J 37/22* (2006.01)
(Continued)

(52) U.S. Cl.
CPC ............ *H01J 37/28* (2013.01); *G01N 1/06* (2013.01); *G01N 23/2252* (2013.01); *G01N 23/2254* (2013.01); *H01J 37/153* (2013.01); *H01J 37/222* (2013.01); *H01J 37/224* (2013.01); *G01N 2223/418* (2013.01); *H01J 2237/024* (2013.01); *H01J 2237/151* (2013.01);
(Continued)

(58) Field of Classification Search
CPC ........ H01J 37/28; H01J 37/153; H01J 37/222; H01J 37/224; H01J 2237/20214; H01J 2237/221; H01J 2237/226; G01N 23/2254; G01N 2223/418
USPC ........................................ 250/492.1, 492.3
See application file for complete search history.

(56) References Cited

U.S. PATENT DOCUMENTS

| 3,872,759 A | 3/1975 | Jackson |
| 2004/0036031 A1 | 2/2004 | Rose et al. |

(Continued)

FOREIGN PATENT DOCUMENTS

| DE | 2 411 535 | 9/1974 |
| DE | 196 06 969 C2 | 8/1997 |

(Continued)

*Primary Examiner* — Nicole M Ippolito
(74) *Attorney, Agent, or Firm* — Muirhead and Saturnelli, LLC

(57) ABSTRACT

The system described herein relates to an object preparation device for preparing an object in a particle beam apparatus. By way of example, the particle beam apparatus is an electron beam apparatus and/or an ion beam apparatus. The system described herein moreover relates to a particle beam apparatus having such an object preparation device and to a method for operating the particle beam apparatus. The object preparation device may have an object receptacle device for receiving the object, a cutting device and a cutting bevel for cutting the object, wherein the cutting bevel may be arranged at the cutting device. The cutting bevel may lay in a cutting plane. Further, an axis of rotation may lay in the cutting plane. The cutting bevel may be embodied to be rotatable about the axis of rotation.

13 Claims, 13 Drawing Sheets

(51) Int. Cl.
*H01J 37/153* (2006.01)
*G01N 23/2252* (2018.01)
*G01N 23/2254* (2018.01)
*G01N 1/06* (2006.01)

(52) U.S. Cl.
CPC .............. *H01J 2237/152* (2013.01); *H01J 2237/20214* (2013.01); *H01J 2237/221* (2013.01); *H01J 2237/226* (2013.01); *H01J 2237/2801* (2013.01)

(56) References Cited

U.S. PATENT DOCUMENTS

| | | |
|---|---|---|
| 2004/0261597 A1 | 12/2004 | Thiem et al. |
| 2006/0234508 A1* | 10/2006 | Shirakashi ........ H01L 21/67173 438/691 |
| 2013/0140459 A1 | 6/2013 | Galloway |
| 2014/0092230 A1 | 4/2014 | Langer et al. |
| 2017/0330724 A1 | 11/2017 | Okumura et al. |

FOREIGN PATENT DOCUMENTS

| | | |
|---|---|---|
| DE | 10 2004 004 355 B3 | 1/2005 |
| DE | 10 2012 217 761 A1 | 4/2014 |
| DE | 11 2015 004 746 T5 | 8/2017 |
| WO | WO 2002/067286 A2 | 8/2002 |
| WO | WO 2008/066846 A2 | 6/2008 |
| WO | WO 2015/175525 A1 | 11/2015 |

\* cited by examiner

OBJECT PREPARATION DEVICE AND PARTICLE BEAM DEVICE HAVING AN OBJECT PREPARATION DEVICE AND METHOD FOR OPERATING THE PARTICLE BEAM DEVICE

TECHNICAL FIELD

The system described herein relates to an object preparation device for preparing an object in a particle beam apparatus. By way of example, the particle beam apparatus may be an electron beam apparatus and/or an ion beam apparatus. The system described herein moreover relates to a particle beam apparatus having such an object preparation device and to a method for operating the particle beam apparatus.

BACKGROUND OF THE INVENTION

Electron beam apparatuses, in particular a scanning electron microscope (also referred to as SEM below) and/or a transmission electron microscope (also referred to as TEM below), are used to examine objects (also referred to as specimens) in order to obtain knowledge in respect of the properties and behaviors of the objects under certain conditions.

In an SEM, an electron beam (also referred to as primary electron beam below) is generated by means of a beam generator and focused on an object to be examined by way of a beam-guiding system. An objective lens is used for focusing purposes. The primary electron beam is guided in a grid-shaped manner over a surface of the object to be examined by way of a deflection device. Here, the electrons of the primary electron beam interact with the object to be examined. In particular interaction particles and/or interaction radiation is/are generated as a result of the interaction. By way of example, the interaction particles are electrons. In particular, electrons are emitted by the object—the so-called secondary electrons—and electrons of the primary electron beam are scattered back—the so-called backscattered electrons. The interaction particles form the so-called secondary beam and they are detected by at least one particle detector. The particle detector generates detection signals which are used to generate an image of the object. An imaging of the object to be examined is thus obtained.

By way of example, the interaction radiation is x-ray radiation or cathodoluminescence. It is detected for example with a radiation detector and is used in particular for examining the material composition of the object.

In the case of a TEM, a primary electron beam is likewise generated by means of a beam generator and focused on an object to be examined by means of a beam-guiding system. The primary electron beam passes through the object to be examined. When the primary electron beam passes through the object to be examined, the electrons of the primary electron beam interact with the material of the object to be examined. The electrons passing through the object to be examined are imaged onto a luminescent screen or onto a detector—for example in the form of a camera—by a system comprising an objective lens. By way of example, the aforementioned system additionally also comprises a projection lens. Here, imaging may also take place in the scanning mode of a TEM. As a rule, such a TEM is referred to as STEM. Additionally, provision can be made for detecting electrons scattered back at the object to be examined and/or secondary electrons emitted by the object to be examined by means of a further detector in order to image an object to be examined.

The integration of the function of an STEM and an SEM in a single particle beam apparatus is known. It is therefore possible to carry out examinations of objects with an SEM function and/or with an STEM function using this particle beam apparatus.

Furthermore, the prior art has disclosed the practice of analyzing and/or processing an object in a particle beam apparatus using, on the one hand, electrons and, on the other hand, ions. By way of example, an electron beam column having the function of an SEM is arranged at the particle beam apparatus. Additionally, an ion beam column is arranged at the particle beam apparatus. Ions used for processing an object are generated by means of an ion beam generator arranged in the ion beam column. By way of example, material of the object is ablated or material is applied onto the object during the processing. The ions are used, additionally or alternatively, for imaging. The electron beam column with the SEM function serves, in particular, for examining further the processed or unprocessed object, but also for processing the object.

The aforementioned particle beam apparatuses of the prior art each have a specimen chamber in which an object that is to be analyzed and/or processed is arranged on a specimen stage. It is furthermore known to arrange a plurality of different objects simultaneously at the specimen stage so as to analyze and/or process them one after the other using the respective particle beam apparatus that has the specimen chamber. The specimen stage is embodied to be movable so as to position the object or objects in the specimen chamber. A relative position of the object or objects with respect to an objective lens is set, for example. A known specimen stage is embodied to be movable in three directions which are arranged perpendicular to one another. Moreover, the specimen stage can be rotated about two rotational axes which are arranged perpendicular to one another.

It is known to operate the specimen chamber in different pressure ranges. For example, the specimen chamber is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber is vacuum-sealed during an examination of the object or objects with the particle beam apparatus.

In order to prepare an object for an examination in a particle beam apparatus, the use of a cutting appliance in the form of a microtome is known. Accordingly, the object is prepared by cutting by means of the microtome. Therefore, the microtome is an object preparation device. The microtome has a knife with a cutting bevel. Layers of the object are cut off the object by the knife. Here, the thickness of the layers lies in the range of 5 nm to 100 μm, for example. The cut-off layers and/or an area of the object exposed by cutting is/are examined in a particle beam apparatus, for example in an SEM. Typically, biological material is prepared using the microtome. Since, as a rule, biological material has a soft embodiment, the biological material to be examined is embedded in a liquid artificial resin. The artificial resin is cured and consequently rendered cuttable. The biological material embedded in the artificial resin is introduced into the microtome. Then, layers of the biological material are ablated using the microtome and examined in the particle beam apparatus. As an alternative thereto, the exposed areas of the biological material are examined.

The practice of performing the preparation of objects by means of a microtome not only prior to introducing the objects into the specimen chamber of a particle beam apparatus but also in the specimen chamber of a particle beam apparatus itself is known. To this end, the arrangement of a microtome in the specimen chamber of a particle beam apparatus in the form of an SEM is known. A microtome that is arranged in the specimen chamber of a particle beam apparatus is also referred to as an "in situ microtome". Using this known microtome, a layer of the object to be examined is cut, in the specimen chamber that is under vacuum, in such a way that an area to be examined is exposed. This exposed area is then examined using the particle beam of the SEM and imaged by generating an image of the exposed area. The aforementioned steps—specifically exposing an area by cutting material off the object and imaging the exposed area—can be repeated multiple times in succession in order to expose areas anew, which are then examined and imaged using the particle beam of the SEM. In this way, one image is generated in each case of each exposed area. The generated images can be used to create a 3D reconstruction of the object to be examined.

In order to obtain good imaging, the practice of aligning the areas exposed by the microtome perpendicular to the beam axis of the SEM when imaging the areas using the particle beam of the SEM is known. Moreover, the exposed areas should be positionable in the SEM in such a way that an acceptable working distance can be obtained between the objective lens of the SEM and the exposed areas. By way of example, the working distance should lie in the range of 1 mm to 5 mm. In order to obtain a perpendicular alignment of the exposed areas in relation to the beam axis of the SEM and in order to obtain a good working distance of the exposed areas from the objective lens, the practice of arranging the microtome on the adjustable specimen stage of the SEM in the specimen chamber is known. As an alternative thereto, the arrangement of a further adjustable stage for the microtome in the specimen chamber in addition to the specimen stage, the microtome being attached to said further adjustable stage, is known.

The prior art has disclosed a microtome that has a base plate and a stand arranged at the base plate. The stand is embodied as an object receptacle, at which an object to be examined is arranged. Moreover, the stand is embodied to be movable from a first position in the form of an imaging position to a second position in the form of a cutting position by way of rotation about an axis. The axis is arranged perpendicular to the optical axis of a particle beam apparatus. The known microtome has a knife that can be used to remove layers of the object and that is arranged at the cutting position of the stand. In the known microtome, the stand and consequently also the object are rotated in the direction of the cutting position by way of a rotation of the stand in a first direction (counterclockwise, for example). In the cutting position of the stand, the object strikes the knife such that a layer of the object is cut off by the knife and an area of the object is exposed. Thereupon, the stand is rotated further in the first direction in order to remove cut material that remains on the knife by way of rubbing the knife against a cleaning material. Subsequently, the stand and consequently also the object are rotated into the imaging position in a second direction (clockwise, for example). In the imaging position, the object with the exposed area is moved in the direction of the objective lens in order to set a desired working distance. As an alternative thereto, the objective lens is refocused on the exposed area. Following this, the exposed area of the object is imaged by means of the particle beam of the SEM.

As already mentioned above, it is desirable for the exposed area to be aligned perpendicular to the particle beam in order to obtain good imaging. However, on account of the arrangement of the microtome in the particle beam apparatus, it is possible that the exposed area is not aligned perpendicular to the particle beam of the particle beam apparatus. By way of example, this may be the case if the exposed area is aligned perpendicular to the vertical direction but a particle beam column of the particle beam apparatus is arranged with a tilt to the vertical.

In respect of the prior art, reference is made in an illustrative manner to WO 2015/175525 A1 and WO 2008/066846 A2.

SUMMARY OF THE INVENTION

The system described herein may provide an object preparation device and a particle beam apparatus with an object preparation device, which ensure that an area of an object that is exposed by the object preparation device is always aligned perpendicular or substantially perpendicular to a particle beam of the particle beam apparatus.

The object preparation device according to the system described herein may be provided for preparing an object in a particle beam apparatus. The object preparation device according to the system described herein has an object receptacle device. The object receptacle device serves to receive the object. The object preparation device further has at least one cutting device that may be provided with a cutting bevel. Expressed differently, the cutting bevel may be arranged at the cutting device. The cutting bevel may be a sharpening on the cutting device which provides the cutting device with its cutting ability. Accordingly, the cutting bevel serves to cut the object. Using the cutting bevel of the cutting device, it may be possible to cut layers of the object from the object. By way of example, the thickness of the cut-off layers lies in the range from 5 nm to 100 μm, including the range boundaries. However, the system described herein is not restricted to the aforementioned range. Instead, the cutting device of the object preparation device according to the system described herein can be used to cut off layers with any thickness that are suitable for the system described herein.

Further provision may be made in the object preparation device according to the system described herein for the cutting bevel to lie in a cutting plane. Expressed differently, the cutting plane may be provided by that plane in which the cutting bevel may be moved in a linear fashion or substantially in a linear fashion, for example. This is explained in more detail below.

The object preparation device according to the system described herein has an axis of rotation, which lies in the cutting plane. In particular, provision may be made for the axis of rotation to be aligned perpendicular or substantially perpendicular to the cutting bevel. The cutting bevel may be embodied to be rotatable about the axis of rotation. Expressed differently, the cutting bevel can be rotated through an angle of rotation into a predeterminable position about the axis of rotation.

Accordingly, provision may be made in the object preparation device according to the system described herein for the cutting bevel to be positioned and to be rotated through the angle of rotation. The angle of rotation may be selected in such a way that the area of the object that is exposed after a cutting process with the cutting device—i.e. with the cutting bevel—is always aligned perpendicular to the optical axis of the particle beam apparatus along which the particle beam of the particle beam apparatus is guided for examining and/or imaging the exposed area. This ensures good imaging and analysis of the exposed area using the particle beam. The cutting bevel may be moved relative to the object along the cutting plane for the purposes of exposing an area. By way of example, the cutting bevel is moved. Additionally, or as an alternative thereto, provision is made for the object to be moved.

Using the object preparation device according to the system described herein, it may be possible to create a 3D reconstruction of the object to be examined by repeated exposure of an area by cutting material off the object and by imaging the exposed area. To this end, the object preparation device, for example, can be moved in the direction of the cutting bevel by means of an object stage (also referred to as specimen stage below) in such a way that a further layer of the object can be removed by means of the cutting bevel. This is discussed below.

In an embodiment of the object preparation device according to the system described herein, provision is made, additionally or alternatively, for the cutting bevel to be embodied to be movable in a linear fashion. In particular, provision may be made for the cutting bevel and the object receptacle device to be movable in a linear fashion relative to one another in the direction of the axis of rotation. As an alternative thereto, provision may be made for the cutting bevel to be moved virtually in linear fashion. In this alternative embodiment, the cutting bevel may be arranged at a long lever arm, for example, said lever arm being rotated about a lever arm axis. The cutting bevel may be moved along a circular trajectory on account of the long lever arm. However, this movement may be substantially linear between two positions on the circular trajectory that are arranged very close together, for example at a distance of a few μm, in particular at a distance of less than 100 μm. Consequently, both the linear movement and the substantially linear movement of the cutting bevel may be performed in the cutting plane.

In a further embodiment of the object preparation device according to the system described herein, provision is made, additionally or alternatively, for an axis, which is always referred to as device axis below, to extend through the object preparation device according to the system described herein. By way of example, the device axis may be embodied as an optical axis of the particle beam apparatus. The optical axis may be also referred to as a beam axis. Additionally, or alternatively, provision may be made for the device axis to be embodied as one of several beam axes of the particle beam apparatus, wherein, for example, the particle beam apparatus has a first particle beam column with a first beam axis and a second particle beam column with a second beam axis. Consequently, the device axis may be either the first beam axis or the second beam axis in this embodiment. The cutting plane includes an angle with the device axis. This angle is different from 0°. Further, the angle may be less than or equal to 90°. Further, provision may be additionally or alternatively made for e.g. a surface of the object to be aligned perpendicular to the device axis. In particular, provision may be made for the surface of the object and the cutting plane to be arranged in different planes. By way of example, the cutting plane may be arranged in a first plane. Further, the surface may be arranged in a second plane, for example. The first plane may be arranged in relation to the second plane in such a way that the first plane and the second plane include the aforementioned angle through which the cutting bevel may be rotated.

In a further embodiment of the object preparation device according to the system described herein, provision is made, additionally or alternatively, for the object receptacle device to have a movable embodiment. In particular, provision may be made for the object receptacle device itself to have a movable embodiment relative to the further structural units of the object preparation device. By moving the object receptacle device, it is possible, for example, to initially rotate the object and to subsequently ablate layers of the object by means of the cutting bevel. This is advantageous in the case of objects with a column-shaped embodiment, in particular, said objects having an object axis that extends through a center of the object, for example. By moving the object receptacle device, it is possible to ablate layers of the object uniformly along the object axis in such a way that layers are ablated along the entire object axis and the object can consequently be examined completely and uniformly. In particular, in this embodiment, it is possible to create a 3D reconstruction of the object to be examined along the entire object axis by repeated exposure of an area by cutting material off the object and by imaging the exposed area.

In a yet further embodiment of the object preparation device according to the system described herein, provision is made, additionally or alternatively, for the object preparation device to have at least one first adjustment unit for rotating the cutting bevel about a first rotation axis in the form of the axis of rotation. Additionally, or alternatively, provision is made for the object preparation device according to the system described herein to have a second adjustment unit for rotating the object receptacle device about a second rotation axis in the form of an object receptacle rotation axis. By way of example, the first rotation axis and the second rotation axis are aligned parallel to one another. Further, provision is made, for example, for the first adjustment unit and/or the second adjustment unit to be embodied as piezo-actuators or as stepper motors. The system described herein is not restricted to such an embodiment of the first adjustment unit and/or of the second adjustment unit. Rather, the first adjustment unit and the second adjustment unit can have any configuration that is suitable for the system described herein.

In an embodiment of the object preparation device according to the system described herein, provision is made, additionally or alternatively, for the object preparation device to be mountable on a movably embodied specimen stage of the particle beam apparatus. Consequently, the object preparation device according to the system described herein can be arranged at the specimen stage that is already arranged in a specimen chamber of the particle beam apparatus. Consequently, the object preparation device may be movable as a whole, for example. By way of example, the specimen stage is embodied to be movable along a first stage axis, a second stage axis and/or a third stage axis, wherein the first stage axis, the second stage axis and the third stage axis are aligned perpendicular to one another. In a further embodiment, provision is made, additionally or alternatively, for the specimen stage to be embodied to be rotatable about a first stage rotation axis and/or about a second stage rotation axis, wherein the first stage rotation axis is aligned perpendicular to the second stage rotation axis. In a further embodiment, in turn, provision is alternatively made for the object preparation device according to the system described herein to be able to be arranged at a movement stage that is arranged in the specimen chamber of the particle beam apparatus in addition to the specimen stage. Consequently, the specimen chamber of the particle beam apparatus may have both the specimen stage and the movement stage.

The system described herein also relates to a particle beam apparatus. By way of example, the particle beam apparatus according to the system described herein is embodied as an electron beam apparatus and/or as an ion beam apparatus. The particle beam apparatus according to the system described herein serves for analyzing, in particular for imaging, and/or for processing an object. The particle beam apparatus according to the system described herein may have at least one beam generator for generating a particle beam comprising charged primary particles. By way of example, the primary particles are electrons or ions. The particle beam apparatus according to the system described herein furthermore may have at least one objective lens for focusing the particle beam onto the object, wherein interaction particles and/or interaction radiation is/are generated upon interaction between the particle beam and the object. The interaction particles are, for example, secondary particles, in particular secondary electrons, and/or backscattered particles, for example backscattered electrons. By way of example, the interaction radiation is x-ray radiation or cathodoluminescence. Further, the particle beam apparatus according to the system described herein may have at least one optical axis, along which the particle beam can be guided. Moreover, the particle beam apparatus according to the system described herein may have at least one detector for detecting the interaction particles and/or interaction radiation. The particle beam apparatus according to the system described herein also may have at least one object preparation device, wherein the object preparation device may have at least one of the features specified above or yet to be specified below or a combination of at least two of the features specified above or yet to be specified below. Further, provision may be made for e.g. the optical axis to be aligned perpendicular to the cutting plane.

In an embodiment of the particle beam apparatus according to the system described herein, provision is made, additionally or alternatively, for the particle beam apparatus to have one of the following features:
(i) the object preparation device is arranged at a movably embodied specimen stage of the particle beam apparatus, wherein the specimen stage is embodied to be movable along a first stage axis, a second stage axis and/or a third stage axis, wherein the first stage axis, the second stage axis and the third stage axis are aligned perpendicular to one another;
(ii) the object preparation device is arranged at a movably embodied specimen stage of the particle beam apparatus, wherein the specimen stage is embodied to be movable along a first stage axis, a second stage axis and/or a third stage axis, wherein the first stage axis, the second stage axis and the third stage axis are aligned perpendicular to one another, wherein the specimen stage is embodied to be rotatable about a first stage rotation axis and/or about a second stage rotation axis, wherein the first stage rotation axis is aligned perpendicular to the second stage rotation axis.

In a yet further embodiment of the particle beam apparatus according to the system described herein, provision is made, additionally or alternatively, for the particle beam apparatus to have at least one mirror corrector for correcting chromatic and/or spherical aberration.

As already mentioned above, provision may be made, additionally or alternatively, in an embodiment of the particle beam apparatus according to the system described herein for the particle beam apparatus to be embodied as an electron beam apparatus and/or as an ion beam apparatus.

In yet a further embodiment of the particle beam apparatus according to the system described herein, provision is made, additionally or alternatively, for the beam generator for generating a particle beam comprising charged primary particles to be embodied as a first beam generator for generating a first particle beam comprising first charged primary particles and for the objective lens to be embodied as a first objective lens for focusing the first particle beam onto the object. Furthermore, the particle beam apparatus may have at least one second beam generator for generating a second particle beam comprising second charged primary particles, and at least one second objective lens for focusing the second particle beam onto the object. The second charged primary particles are electrons or ions, for example.

In a further embodiment of the particle beam apparatus according to the system described herein, in turn, provision is made, additionally or alternatively, for the first beam generator and the first objective lens to be arranged in a first particle beam column, wherein the first particle beam column has a first beam axis. By way of example, the first particle beam column is embodied as an electron beam column or ion beam column. Further, provision may be made for e.g. the second beam generator and the second objective lens to be arranged in a second particle beam column, wherein the second particle beam column has a second beam axis. By way of example, the second particle beam column is embodied as an electron beam column or ion beam column. The first beam axis and the second beam axis include a beam axis angle that differs from 0° and 180°. By way of example, it lies in the range from 40° to 60°, including the range boundaries. In particular, provision may be made for the first particle beam column to be arranged in relation to the second particle beam column at an angle of approximately 50° to 55°. Further, provision may be made for the cutting plane to be aligned perpendicular to the first beam axis in a first position of the cutting device and for the cutting plane to be aligned perpendicular to the second beam axis in a second position of the cutting device.

The system described herein also relates to a method for operating the particle beam apparatus, having at least one of the features specified further above or yet to be specified below or with a combination of at least two of the features specified further above or yet to be specified below. In the method according to the system described herein, provision may be made for the cutting bevel to be rotated about the axis of rotation into a position in which the cutting plane may be aligned perpendicular to the optical axis of the particle beam apparatus. In particular, provision may be made for the axis of rotation to be aligned perpendicular or substantially perpendicular to the cutting bevel. Here, the cutting bevel may be rotated by rotation through an angle of rotation. Further, the cutting bevel may be moved relative to the object in the cutting plane. By way of example, the cutting bevel may be moved. Provision may be made, additionally or alternatively, for the object to be moved. By way of example, there is a linear movement of the cutting bevel or a substantially linear movement of the cutting bevel in the cutting plane, as already explained above. A layer of the object may be ablated by moving the cutting bevel. As a result of this, an area may be exposed, which area can be irradiated by the particle beam of the particle beam apparatus. In particular, provision may be made for imaging and/or an analysis of the exposed area to be carried out by means of the particle beam. The method according to the system described herein has the same advantages as specified above.

In an embodiment of the method according to the system described herein, provision is made, additionally or alternatively, for the object receptacle device to be rotated through an object receptacle angle of rotation. By way of example, the object receptacle device is rotated about the second rotation axis. By moving the object receptacle device, it is possible to initially rotate the object and to subsequently ablate layers of the object by means of the cutting bevel. This is advantageous in the case of objects with a column-shaped embodiment, in particular, as already mentioned above.

BRIEF DESCRIPTION OF THE DRAWINGS

The system described herein will be explained in more detail below on the basis of illustrative embodiments using drawings. In the figures.

DESCRIPTION OF VARIOUS EMBODIMENTS

The system described herein is now explained in more detail by means of particle beam apparatuses in the form of an SEM and in the form of a combination apparatus, which may have an electron beam column and an ion beam column. The system described herein may be used in any particle beam apparatus, in particular in every electron beam apparatus and/or in every ion beam apparatus.

Figure 1:
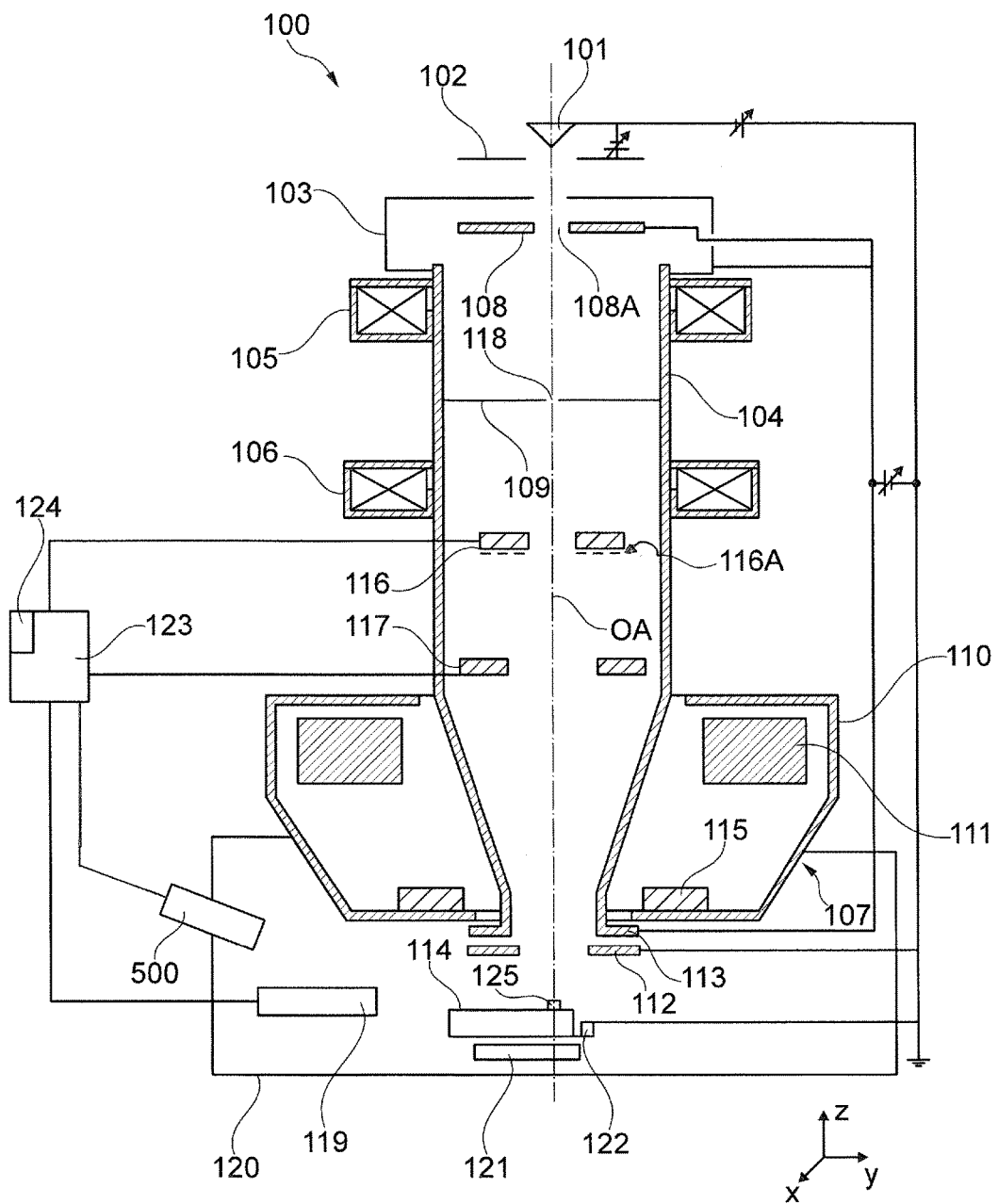
FIG. 1 shows a first illustrative embodiment of a particle beam apparatus.

FIG. 1 shows a schematic illustration of an SEM 100, according to an illustrative embodiment of the system described herein. The SEM 100 comprises a first beam generator in the form of an electron source 101, which may be embodied as a cathode. Further, the SEM 100 may be provided with an extraction electrode 102 and with an anode 103, which may be placed onto one end of a beam-guiding tube 104 of the SEM 100. By way of example, the electron source 101 is embodied as a thermal field emitter. However, the system described herein is not restricted to such an electron source 101. Rather, any electron source is utilizable.

Electrons emerging from the electron source 101 form a primary electron beam. The electrons may be accelerated to the anode potential due to a potential difference between the electron source 101 and the anode 103. In the illustrative embodiment depicted here, the anode potential is 1 kV to 20 kV, e.g. 5 kV to 15 kV, in particular 8 kV, in relation to a ground potential of a housing of a specimen chamber 120. However, alternatively it could be at ground potential.

Two condenser lenses, namely a first condenser lens 105 and a second condenser lens 106, may be arranged at the beam-guiding tube 104. Here, proceeding from the electron source 101 as viewed in the direction of a first objective lens 107, the first condenser lens 105 is arranged first, followed by the second condenser lens 106. Further illustrative embodiments of the SEM 100 may have only a single condenser lens. A first aperture unit 108 may be arranged between the anode 103 and the first condenser lens 105. Together with the anode 103 and the beam-guiding tube 104, the first aperture unit 108 may be at a high voltage potential, namely the potential of the anode 103, or it is connected to ground. The first stop unit 108 may have numerous first apertures 108A, of which one is depicted in FIG. 1. Two first apertures 108A may be present, for example. Each one of the numerous first apertures 108A may have a different aperture diameter. By means of an adjustment mechanism (not depicted here), it may be possible to set a desired first aperture 108A onto an optical axis OA of the SEM 100. In further illustrative embodiments, the first aperture unit 108 may be provided with only a single aperture 108A. In this illustrative embodiment, an adjustment mechanism may be omitted. The first aperture unit 108 is then designed in a stationary fashion. A stationary second aperture unit 109 is arranged between the first condenser lens 105 and the second condenser lens 106. As an alternative thereto, provision is made for the second aperture unit 109 to be embodied in a movable fashion.

The first objective lens 107 may have pole pieces 110, in which a bore may be formed. The beam-guiding tube 104 may be guided through this bore. A coil 111 may be arranged in the pole pieces 110.

An electrostatic retardation device may be arranged in a lower region of the beam-guiding tube 104. It may have a single electrode 112 and a tube electrode 113. The tube electrode 113 may be arranged at one end of the beam-guiding tube 104, which faces an object 125 that may be arranged in an object preparation device in the form of a microtome 114. The microtome 114 is explained in more detail below. Together with the beam-guiding tube 104, the tube electrode 113 may be at the potential of the anode 103, while the single electrode 112 and the object 125 may be at a lower potential in relation to the potential of the anode 103. In the present case, this is the ground potential of the housing of the specimen chamber 120. In this manner, the electrons of the primary electron beam may be decelerated to a desired energy which may be required for examining the object 125.

The SEM 100 further comprises a scanning device 115, by means of which the primary electron beam may be deflected and scanned over the object 125. Here, the electrons of the primary electron beam interact with the object 125. As a result of the interaction, interaction particles may be generated, which may be detected. In particular, electrons may be emitted from the surface of the object 125—the so-called secondary electrons—or electrons of the primary electron beam may be scattered back—the so-called backscattered electrons—as interaction particles.

The object 125 and the single electrode 112 may also be at different potentials and potentials different than ground. It is thereby possible to set the location of the retardation of the primary electron beam in relation to the object 125. By way of example, if the retardation is carried out quite close to the object 125, imaging aberrations become smaller.

A detector arrangement comprising a first detector 116 and a second detector 117 may be arranged in the beam-guiding tube 104 for detecting the secondary electrons and/or the backscattered electrons. Here, the first detector 116 may be arranged on the source-side along the optical axis OA, while the second detector 117 may be arranged on the object-side along the optical axis OA in the beam-guiding tube 104. The first detector 116 and the second detector 117 may be arranged offset from one another in the direction of the optical axis OA of the SEM 100. Both the first detector 116 and the second detector 117 each may have a passage opening, through which the primary electron beam may pass. The first detector 116 and the second detector 117 may be approximately at the potential of the anode 103 and of the beam-guiding tube 104. The optical axis OA of the SEM 100 extends through the respective passage openings.

The second detector 117 may serve principally for detecting secondary electrons. Upon emerging from the object 125, the secondary electrons initially have a low kinetic energy and arbitrary directions of motion. By means of the strong extraction field emanating from the tube electrode 113, the secondary electrons may be accelerated in the direction of the first objective lens 107. The secondary electrons enter the first objective lens 107 approximately parallel. The beam diameter of the beam of secondary electrons remains small in the first objective lens 107 as well. The first objective lens 107 then may have a strong effect on the secondary electrons and generates a comparatively short focus of the secondary electrons with sufficiently steep angles with respect to the optical axis OA, such that the secondary electrons diverge far apart from one another downstream of the focus and are incident on the second detector 117 on the active area thereof. By contrast, only a small proportion of electrons that are backscattered at the object 125—that is to say backscattered electrons which have a relatively high kinetic energy in comparison with the secondary electrons upon emerging from the object 125—are detected by the second detector 117. The high kinetic energy and the angles of the backscattered electrons with respect to the optical axis OA upon emerging from the object 125 have the effect that a beam waist, that is to say a beam region having a minimum diameter, of the backscattered electrons lies in the vicinity of the second detector 117. A large portion of the backscattered electrons passes through the passage opening of the second detector 117. Therefore, the first detector 116 substantially serves to detect the backscattered electrons.

In a further embodiment of the SEM 100, the first detector 116 may additionally be embodied with an opposing field grating 116A. The opposing field grating 116A may be arranged at the side of the first detector 116 directed toward the object 125. With respect to the potential of the beam-guiding tube 104, the opposing field grating 116A may have a negative potential such that only backscattered electrons with a high energy pass through the opposing field grating 116A to the first detector 116. Additionally or alternatively, the second detector 117 has a further opposing field grating, which has an analogous embodiment to the aforementioned opposing field grating 116A of the first detector 116 and which has an analogous function.

Further, the SEM 100 may have in the specimen chamber 120 a chamber detector 119, for example an Everhart-Thornley detector or an ion detector which has a detection surface that may be coated with metal and blocks light.

The detection signals generated by the first detector 116, the second detector 117 and the chamber detector 119 may be used to generate an image or images of the surface of the object 125.

The first aperture unit 108 and of the second aperture unit 109, as well as the passage openings of the first detector 116 and of the second detector 117 are depicted in exaggerated fashion. The passage openings of the first detector 116 and of the second detector 117 may have an extent perpendicular to the optical axis OA in the range of 0.5 mm to 5 mm. By way of example, they are of circular design and have a diameter in the range of 1 mm to 3 mm perpendicular to the optical axis OA.

The second aperture unit 109 may be configured as a pinhole aperture in the illustrative embodiment depicted here and provided with a second aperture 118 for the passage of the primary electron beam, which may have an extent in the range from 5 µm to 500 µm, e.g. 35 µm. As an alternative thereto, provision is made in a further embodiment for the second aperture unit 109 to be provided with a plurality of apertures, which can be displaced mechanically with respect to the primary electron beam or which can be reached by the primary electron beam by the use of electrical and/or magnetic deflection elements. The second aperture unit 109 may be embodied as a pressure stage unit. It separates a first region, in which the electron source 101 may be arranged and in which an ultra-high vacuum ($10^{-7}$ hPa to $10^{-12}$ hPa) prevails, from a second region, which may have a high vacuum ($10^{-3}$ hPa to $10^{-7}$ hPa). The second region may be the intermediate pressure region of the beam-guiding tube 104, which leads to the specimen chamber 120.

The specimen chamber 120 may be under vacuum. For the purposes of producing the vacuum, a pump (not illustrated) may be arranged at the specimen chamber 120. In the illustrative embodiment illustrated in FIG. 1, the specimen chamber 120 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 120 may be vacuum-sealed.

The microtome 114 may be arranged at a specimen stage 122. The specimen stage 122 may be embodied to be movable in three directions arranged perpendicular to one another, namely in an x-direction (first stage axis), in a y-direction (second stage axis) and in a z-direction (third stage axis). Moreover, the specimen stage 122 can be rotated about two rotational axes which may be arranged perpendicular to one another (stage rotation axes).

The SEM 100 may further comprise a third detector 121, which may be arranged in the specimen chamber 120. More precisely, the third detector 121 may be arranged downstream of the microtome 114, as seen from the electron source 101 along the optical axis OA. The microtome 114 can be rotated in such a way that the object 125 that may be arranged at the microtome 114 can have the primary electron beam radiated therethrough. When the primary electron beam passes through the object 125 to be examined, the electrons of the primary electron beam interact with the material of the object 125 to be examined. The electrons passing through the object 125 to be examined may be detected by the third detector 121.

Arranged at the specimen chamber 120 may be a radiation detector 500, which may be used to detect interaction radiation, for example x-ray radiation and/or cathodoluminescence. The radiation detector 500, the first detector 116, the second detector 117 and the chamber detector 119 may be connected to a monitoring unit 123, which has a monitor 124. The third detector 121 also may be connected to the monitoring unit 123. For reasons of clarity, this is not illustrated. The monitoring unit 123 processes detection signals that are generated by the first detector 116, the second detector 117, the chamber detector 119, the third detector 121 and/or the radiation detector 500 and displays on the monitor 124 said detection signals in the form of images.

Figure 2:
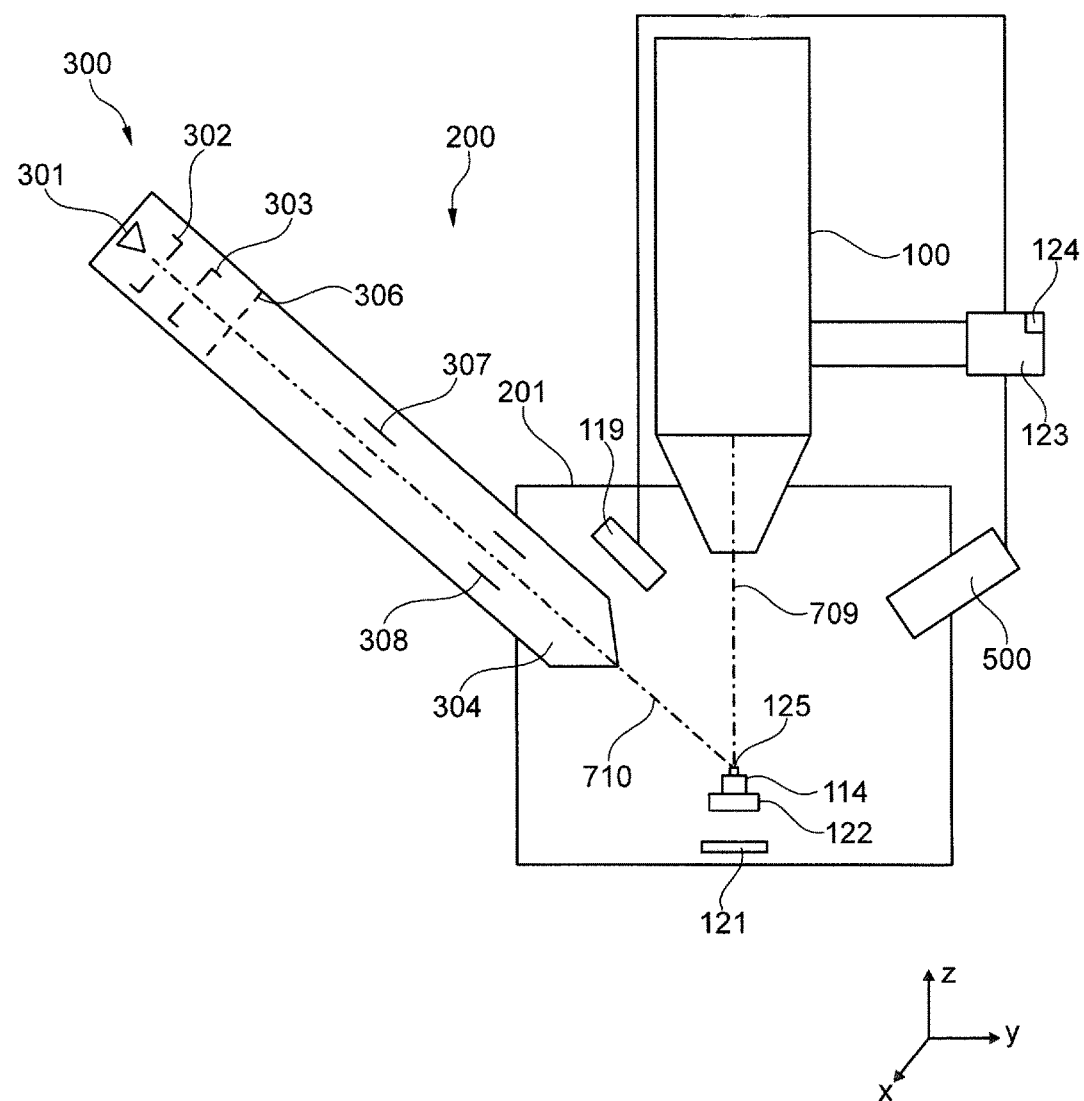
FIG. 2 shows a second illustrative embodiment of a particle beam apparatus.

FIG. 2 shows a particle beam apparatus in the form of a combination apparatus 200, according to an illustrative embodiment of the system described herein. The combination apparatus 200 may have two particle beam columns. On the one hand, the combination apparatus 200 may be provided with the SEM 100, as already depicted in FIG. 1, but without the specimen chamber 120. Rather, the SEM 100 may be arranged at a specimen chamber 201. The specimen chamber 201 may be under vacuum. For the purposes of producing the vacuum, a pump (not illustrated) may be arranged at the specimen chamber 201. In the illustrative embodiment illustrated in FIG. 2, the specimen chamber 201 may be operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 201 may be vacuum-sealed.

Arranged in the specimen chamber 201 may be a chamber detector 119 which may be embodied, for example, in the form of an Everhart-Thornley detector or an ion detector and which has a detection surface coated with metal and which blocks light. Further, the third detector 121 may be arranged in the specimen chamber 201.

The SEM 100 may serve to generate a first particle beam, namely the primary electron beam already described further above, and may have the optical axis, already specified above, which may be provided with reference sign 709 in FIG. 2 and which also may be referred to as first beam axis below. On the other hand, the combination apparatus 200 may be provided with an ion beam apparatus 300, which likewise may be arranged at the specimen chamber 201. The ion beam device 300 likewise has an optical axis, which is provided with the reference sign 710 in FIG. 2 and which is also referred to as second beam axis below.

The SEM 100 may be arranged vertically in relation to the specimen chamber 201. By contrast, the ion beam apparatus 300 may be arranged inclined by an angle of approximately 50° in relation to the SEM 100. It may have a second beam generator in the form of an ion beam generator 301. Ions, which form a second particle beam in the form of an ion beam, are generated by the ion beam generator 301. The ions may be accelerated by means of an extraction electrode 302, which may be at a predeterminable potential. The second particle beam then passes through ion optics of the ion beam apparatus 300, wherein the ion optics comprise a condenser lens 303 and a second objective lens 304. The second objective lens 304 ultimately generates an ion probe, which may be focused on the object 125 arranged in an object preparation device in the form of a microtome 114. The microtome 114 may be arranged at a specimen stage 122.

An adjustable or selectable aperture unit 306, a first electrode arrangement 307 and a second electrode arrangement 308 may be arranged above the second objective lens 304 (i.e. in the direction of the ion beam generator 301), wherein the first electrode arrangement 307 and the second electrode arrangement 308 may be embodied as scanning electrodes. The second particle beam may be scanned over the surface of the object 125 by means of the first electrode arrangement 307 and the second electrode arrangement 308, with the first electrode arrangement 307 acting in a first direction and the second electrode arrangement 308 acting in a second direction, which may be counter to the first direction. Using this, scanning may be carried out in e.g. an x-direction. The scanning in a y-direction perpendicular thereto may be brought about by further electrodes (not depicted here), which may be rotated by 90°, at the first electrode arrangement 307 and at the second electrode arrangement 308.

As discussed above, the microtome 114 may be arranged at the specimen stage 122. In the illustrative embodiment shown in FIG. 2, the specimen stage 122 also may be embodied to be movable in three directions arranged perpendicular to one another, namely in an x-direction (first stage axis), in a y-direction (second stage axis) and in a z-direction (third stage axis). Moreover, the specimen stage 122 can be rotated about two rotational axes which may be arranged perpendicular to one another (stage rotation axes).

The distances depicted in FIG. 2 between the individual units of the combination apparatus 200 are depicted in exaggerated fashion in order to better illustrate the individual units of the combination apparatus 200.

Arranged at the specimen chamber 201 may be a radiation detector 500, which may be used to detect interaction radiation, for example x-ray radiation and/or cathodoluminescence. The radiation detector 500 may be connected to a monitoring unit 123, which has a monitor 124. The monitoring unit 123 processes detection signals that are generated by the first detector 116, the second detector 117 (not illustrated in FIG. 2), the chamber detector 119, the third detector 121 and/or the radiation detector 500 and displays on the monitor 124 said detection signals in the form of images.

Figure 3:
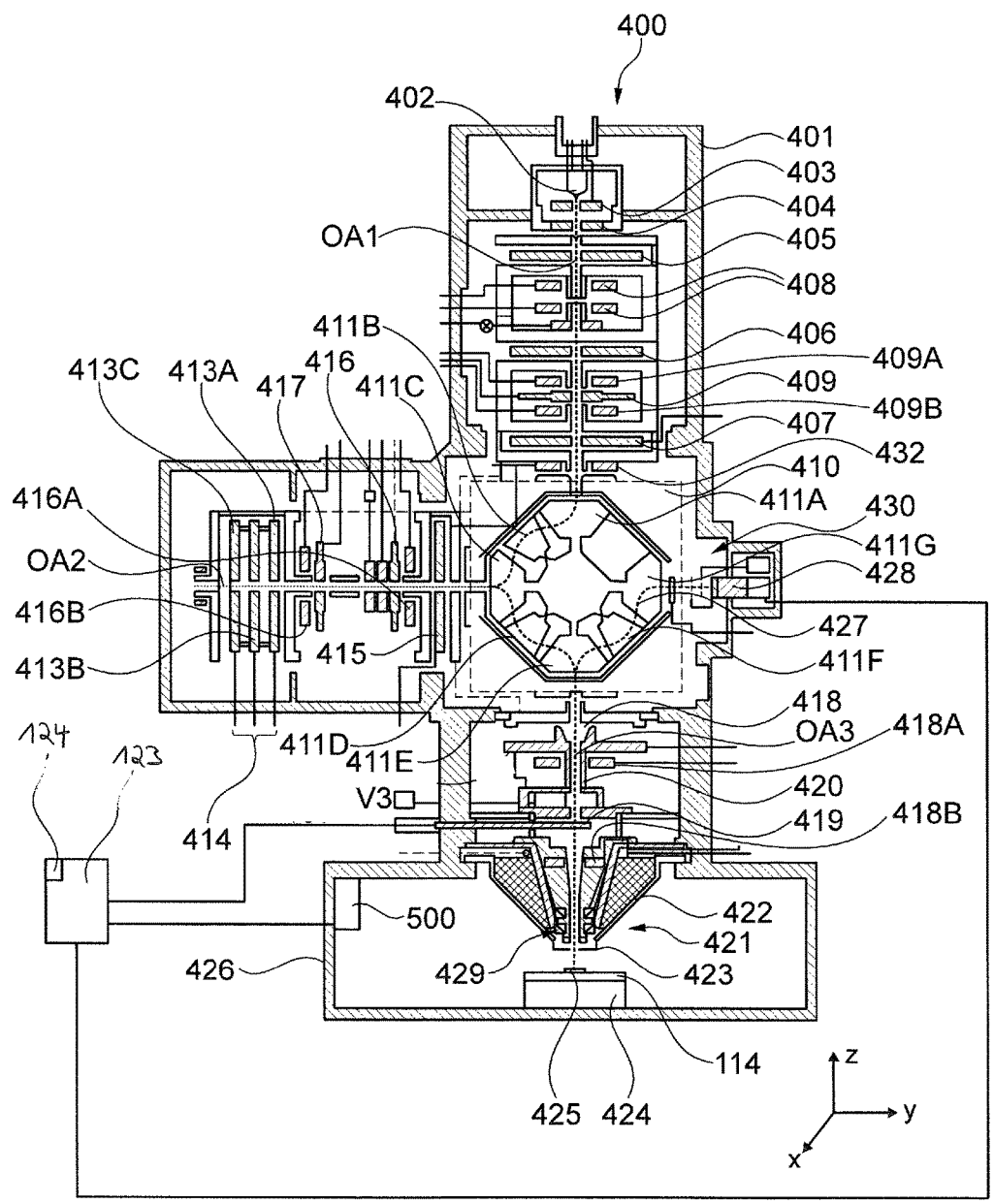
FIG. 3 shows a third illustrative embodiment of a particle beam apparatus.

FIG. 3 is a schematic illustration of a further illustrative embodiment of a particle beam apparatus according to the system described herein. This illustrative embodiment of the particle beam apparatus is provided with the reference sign 400 and said illustrative embodiment comprises a mirror corrector for correcting e.g. chromatic and/or spherical aberrations. The particle beam apparatus 400 comprises a particle beam column 401, which may be embodied as an electron beam column and which substantially corresponds to an electron beam column of a corrected SEM. However, the particle beam apparatus 400 is not restricted to an SEM with a mirror corrector. Rather, the particle beam apparatus may comprise any type of correction units.

The particle beam column 401 comprises a particle beam generator in the form of an electron source 402 (cathode), an extraction electrode 403, and an anode 404. By way of example, the electron source 402 is embodied as a thermal field emitter. Electrons emerging from the electron source 402 may be accelerated to the anode 404 due to a potential difference between the electron source 402 and the anode 404. Accordingly, a particle beam in the form of an electron beam may be formed along a first optical axis OA1.

The particle beam may be guided along a beam path, which corresponds to the first optical axis OA1, after the particle beam has emerged from the electron source 402. A first electrostatic lens 405, a second electrostatic lens 406, and a third electrostatic lens 407 may be used to guide the particle beam.

Furthermore, the particle beam may be adjusted along the beam path using a beam-guiding device. The beam-guiding device of this illustrative embodiment comprises a source adjustment unit with two magnetic deflection units 408 arranged along the first optical axis OA1. Moreover, the particle beam apparatus 400 comprises electrostatic beam deflection units. A first electrostatic beam deflection unit 409, which also may be embodied as a quadrupole in a further embodiment, is arranged between the second electrostatic lens 406 and the third electrostatic lens 407. The first electrostatic beam deflection unit 409 may be likewise arranged downstream of the magnetic deflection units 408. A first multi-pole unit 409A in the form of a first magnetic deflection unit may be arranged at one side of the first electrostatic beam deflection unit 409. Moreover, a second multi-pole unit 409B in the form of a second magnetic deflection unit may be arranged at the other side of the first electrostatic beam deflection unit 409. The first electrostatic beam deflection unit 409, the first multi-pole unit 409A, and the second multi-pole unit 409B may be set for the purposes of setting the particle beam in respect of the axis of the third electrostatic lens 407 and the entrance window of a beam deflection device 410. The first electrostatic beam deflection unit 409, the first multi-pole unit 409A and the second multi-pole unit 409B may interact like a Wien filter. A further magnetic deflection element 432 may be arranged at the entrance to the beam deflection device 410.

The beam deflection device 410 may be used as a particle beam deflector, which deflects the particle beam in a specific manner. The beam deflection device 410 comprises a plurality of magnetic sectors, namely a first magnetic sector 411A, a second magnetic sector 411B, a third magnetic sector 411C, a fourth magnetic sector 411D, a fifth magnetic sector 411E, a sixth magnetic sector 411F, and a seventh magnetic sector 411G. The particle beam enters the beam deflection device 410 along the first optical axis OA1 and said particle beam may be deflected by the beam deflection device 410 in the direction of a second optical axis OA2. The beam deflection may be performed by means of the first magnetic sector 411A, by means of the second magnetic sector 411B and by means of the third magnetic sector 411C through an angle of 30° to 120°. The second optical axis OA2 may be oriented at the same angle with respect to the first optical axis OA1. The beam deflection device 410 also deflects the particle beam which may be guided along the second optical axis OA2, to be precise in the direction of a third optical axis OA3. The beam deflection may be provided by the third magnetic sector 411C, the fourth magnetic sector 411D, and the fifth magnetic sector 411E. In the illustrative embodiment in FIG. 3, the deflection with respect to the second optical axis OA2 and with respect to the third optical axis OA3 is provided by deflecting the particle beam at an angle of 90°. Hence, the third optical axis OA3 extends coaxially with respect to the first optical axis OA1. However, reference is made to the fact that the particle beam apparatus 400 according to the system described herein is not restricted to deflection angles of 90°. Rather, any suitable deflection angle may be selected by the beam deflection device 410, for example 70° or 110°, such that the first optical axis OA1 does not extend coaxially with respect to the third optical axis OA3. In respect of further details of the beam deflection device 410, reference is made to WO 2002/067286 A2.

After the particle beam was deflected by the first magnetic sector 411A, the second magnetic sector 411B, and the third magnetic sector 411C, the particle beam may be guided along the second optical axis OA2. The particle beam may be guided to an electrostatic mirror 414 and travels on its path to the electrostatic mirror 414 along a fourth electrostatic lens 415, a third multi-pole unit 416A in the form of a magnetic deflection unit, a second electrostatic beam deflection unit 416, a third electrostatic beam deflection unit 417, and a fourth multi-pole unit 416B in the form of a magnetic deflection unit. The electrostatic mirror 414 comprises a first mirror electrode 413A, a second mirror electrode 413B, and a third mirror electrode 413C. Electrons of the particle beam which are reflected back at the electrostatic mirror 414 once again travel along the second optical axis OA2 and re-enter the beam deflection device 410. Then, they may be deflected to the third optical axis OA3 by the third magnetic sector 411C, the fourth magnetic sector 411D, and the fifth magnetic sector 411E.

The electrons of the particle beam emerge from the beam deflection device 410 and said electrons may be guided along the third optical axis OA3 to an object 425 that may be intended to be examined and arranged in an object preparation device in the form of a microtome 114. On the path to the object 425, the particle beam may be guided to a fifth electrostatic lens 418, a beam-guiding tube 420, a fifth multi-pole unit 418A, a sixth multi-pole unit 418B, and an objective lens 421. The fifth electrostatic lens 418 may be an electrostatic immersion lens. By way of the fifth electrostatic lens 418, the particle beam may be decelerated or accelerated to an electric potential of the beam-guiding tube 420.

By means of the objective lens 421, the particle beam may be focused in a focal plane in which the object 425 may be arranged. The microtome 114 may be arranged at a movable specimen stage 424. The movable specimen stage 424 may be arranged in a specimen chamber 426 of the particle beam apparatus 400. The specimen stage 424 may be embodied to be movable in three directions arranged perpendicular to one another, namely in an x-direction (first stage axis), in a y-direction (second stage axis) and in a z-direction (third stage axis). Moreover, the specimen stage 424 can be rotated about two rotational axes which may be arranged perpendicular to one another (stage rotation axes).

The specimen chamber 426 may be under vacuum. For the purposes of producing the vacuum, a pump (not illustrated) may be arranged at the specimen chamber 426. In the illustrative embodiment illustrated in FIG. 3, the specimen chamber 426 is operated in a first pressure range or in a second pressure range. The first pressure range comprises only pressures of less than or equal to $10^{-3}$ hPa, and the second pressure range comprises only pressures of greater than $10^{-3}$ hPa. To ensure said pressure ranges, the specimen chamber 426 may be vacuum-sealed.

The objective lens 421 may be embodied as a combination of a magnetic lens 422 and a sixth electrostatic lens 423. The end of the beam-guiding tube 420 further may be an electrode of an electrostatic lens. After emerging from the beam-guiding tube 420, particles of the particle beam apparatus may be decelerated to a potential of the object 425. The objective lens 421 is not restricted to a combination of the magnetic lens 422 and the sixth electrostatic lens 423. Rather, the objective lens 421 may assume any suitable form. By way of example, the objective lens 421 also may be embodied as a purely magnetic lens or as a purely electrostatic lens.

The particle beam which may be focused onto the object 425 interacts with the object 425. Interaction particles are generated. In particular, secondary electrons are emitted from the object 425 or backscattered electrons are scattered back at the object 425. The secondary electrons or the backscattered electrons may be accelerated again and guided into the beam-guiding tube 420 along the third optical axis OA3. In particular, the trajectories of the secondary electrons and the backscattered electrons extend on the route of the beam path of the particle beam in the opposite direction to the particle beam.

The particle beam apparatus 400 comprises a first analysis detector 419 which may be arranged between the beam deflection device 410 and the objective lens 421 along the beam path. Secondary electrons traveling in directions oriented at a large angle with respect to the third optical axis OA3 are detected by the first analysis detector 419. Backscattered electrons and secondary electrons which have a small axial distance with respect to the third optical axis OA3 at the location of the first analysis detector 419—i.e. backscattered electrons and secondary electrons which have a small distance from the third optical axis OA3 at the location of the first analysis detector 419—enter the beam deflection device 410 and may be deflected to a second analysis detector 428 by the fifth magnetic sector 411E, the sixth magnetic sector 411F and the seventh magnetic sector 411G along a detection beam path 427. By way of example, the deflection angle is 90° or 110°.

The first analysis detector 419 generates detection signals which may be largely generated by emitted secondary electrons. The detection signals which are generated by the first analysis detector 419 may be guided to a monitoring unit 123 and used to obtain information about the properties of the interaction region of the focused particle beam with the object 425. In particular, the focused particle beam may be scanned over the object 425 using a scanning device 429. Then, an image of the scanned region of the object 425 can be generated by the detection signals, which may be generated by the first analysis detector 419, and it can be displayed on a display unit. The display unit is for example a monitor 124 that is arranged at the monitoring unit 123.

The second analysis detector 428—also may be connected to the monitoring unit 123. Detection signals of the second analysis detector 428 may be supplied to the monitoring unit 123 and used to generate an image of the scanned region of the object 425 and to display it on a display unit. The display unit is for example the monitor 124 that is arranged at the monitoring unit 123.

Arranged at the specimen chamber 426 may be a radiation detector 500, which may be used to detect interaction radiation, for example x-ray radiation and/or cathodoluminescence. The radiation detector 500 may be connected to the monitoring unit 123, which has the monitor 124. The monitoring unit 123 processes detection signals of the radiation detector 500 and displays them in the form of images on the monitor 124.

Figure 4:
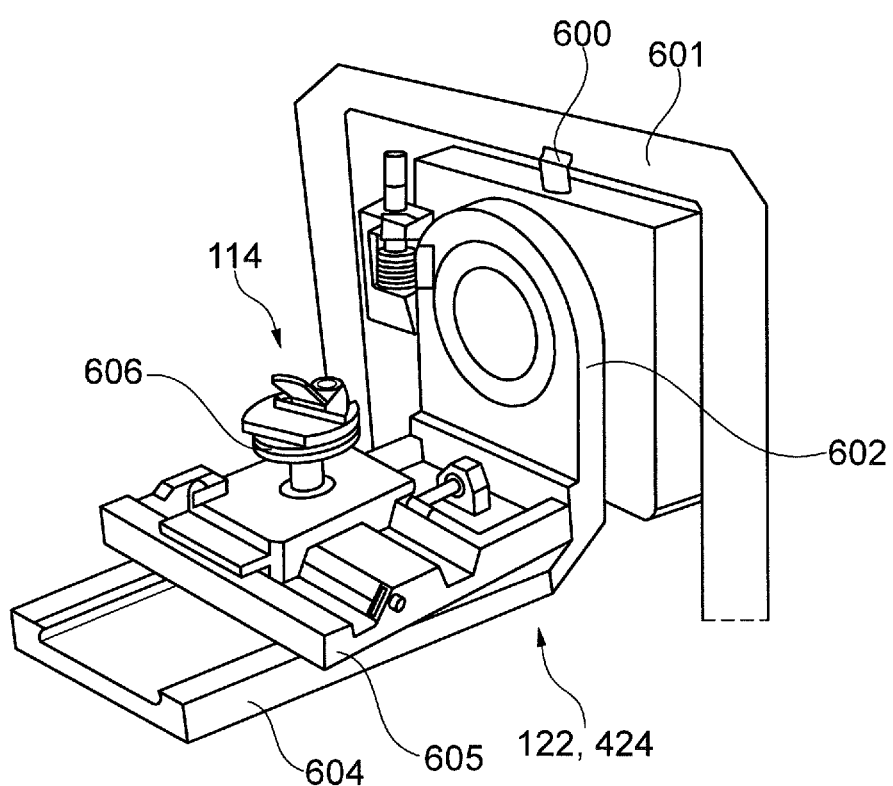
FIG. 4 shows a schematic illustration of an illustrative embodiment of a movably embodied specimen stage for a particle beam apparatus.

Now, the specimen stage 122, 424 of the particle beam apparatuses 100, 200 and 400 explained above is discussed in more detail below. The specimen stage 122, 424 may be embodied as a movable specimen stage, which is illustrated schematically in FIGS. 4 and 5. Reference is made to the fact that the system described herein is not restricted to the specimen stage 122, 424 described here. Rather, the system described herein can have any movable specimen stage that is suitable for the system described herein.

Arranged on the specimen stage 122, 424 may be the microtome 114, in which the object 125, 425 may be arranged in turn. The specimen stage 122, 424 may have movement elements that ensure a movement of the specimen stage 122, 424 in such a way that a region of interest on the object 125, 425 can be examined by means of a particle beam. The movement elements are illustrated schematically in FIGS. 4 and 5 and are explained below.

The specimen stage 122, 424 may have a first movement element 600 at a housing 601 of the specimen chamber 120, 201 or 426, in which the specimen stage 122, 424 may be arranged. The first movement element 600 facilitates a movement of the specimen stage 122, 424 along the z-axis (third stage axis). Further, provision may be made of a second movement element 602. The second movement element 602 facilitates a rotation of the specimen stage 122, 424 about a first stage rotation axis 603, which also may be referred to as a tilt axis. This second movement element 602 serves to tilt an object 125, 425 arranged in the microtome 114 about the first stage rotation axis 603.

Arranged at the second movement element 602, in turn, may be a third movement element 604 that may be embodied as a guide for a carriage and that ensures that the specimen stage 122, 424 may be movable in the x-direction (first stage axis). The aforementioned carriage may be a further movement element in turn, namely a fourth movement element 605. The fourth movement element 605 may be embodied in such a way that the specimen stage 122, 424 is movable in the y-direction (second stage axis). To this end, the fourth movement element 605 may have a guide in which a further carriage may be guided, the microtome 114 in turn being arranged at the latter.

The microtome 114 may be embodied, in turn, with a fifth movement element 606 that facilitates a rotation of the microtome 114 about a second stage rotation axis 607. The second stage rotation axis 607 may be oriented perpendicular to the first stage rotation axis 603.

On account of the above-described arrangement, the specimen stage 122, 424 of the illustrative embodiment discussed here has the following kinematic chain: first movement element 600 (movement along the z-axis)—second movement element 602 (rotation about the first stage rotation axis 603)—third movement element 604 (movement along the x-axis)—fourth movement element 605 (movement along the y-axis)—fifth movement element 606 (rotation about the second stage rotation axis 607).

In a further illustrative embodiment (not illustrated here), provision may be made for further movement elements to be arranged at the specimen stage 122, 424 such that movements along further translational axes and/or about further rotational axes are facilitated.

Figure 5:
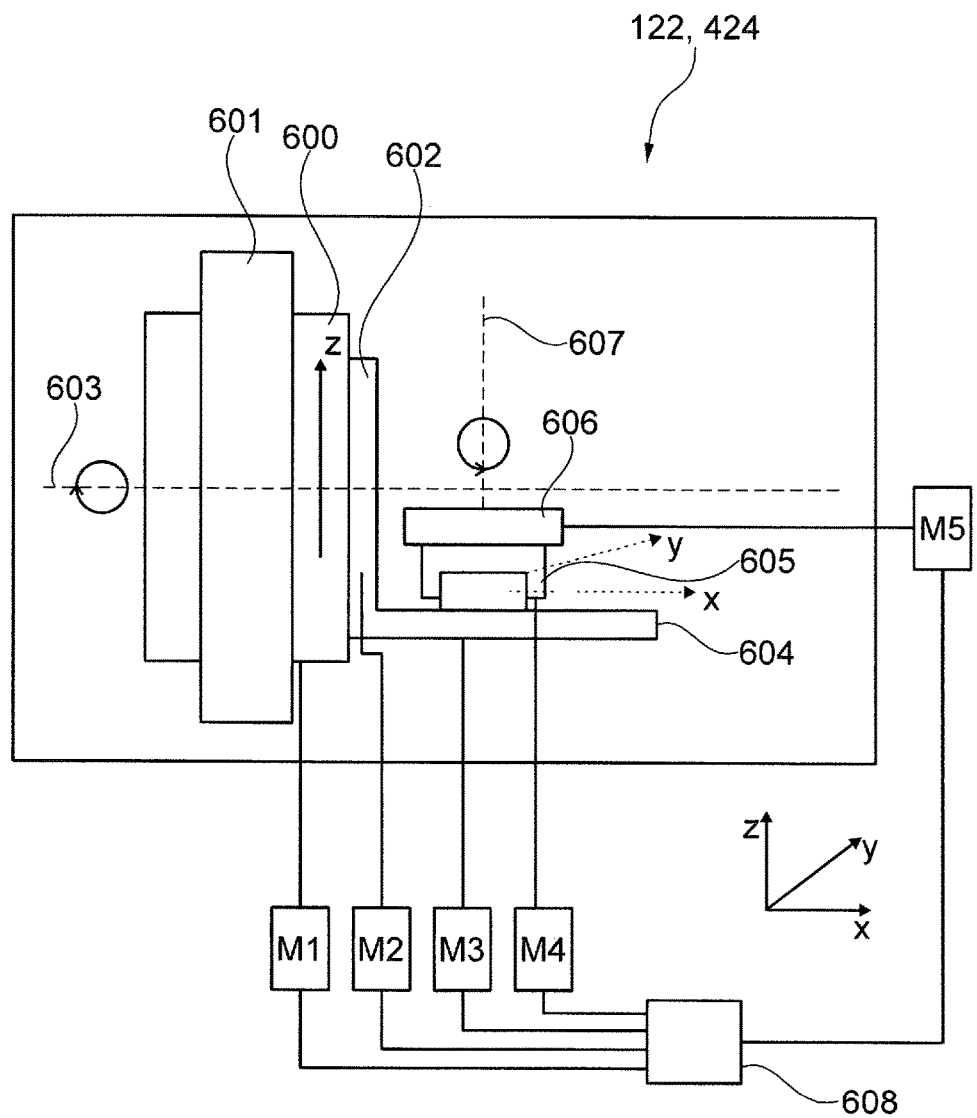
FIG. 5 shows a further schematic illustration of the specimen stage according to FIG. 4, according to an embodiment of the system described herein.

It is clear from FIG. 5 that each of the aforementioned movement elements may be connected to a stepper motor. Thus, the first movement element 600 may be connected to a first stepper motor M1 and the former is driven on account of a driving force that is provided by the first stepper motor M1. The second movement element 602 may be connected to a second stepper motor M2, which drives the second movement element 602. The third movement element 604 may be connected, in turn, to a third stepper motor M3. The third stepper motor M3 provides a driving force for driving the third movement element 604. The fourth movement element 605 may be connected to a fourth stepper motor M4, wherein the fourth stepper motor M4 drives the fourth movement element 605. Further, the fifth movement element 606 may be connected to a fifth stepper motor M5. The fifth stepper motor M5 provides a driving force that drives the fifth movement element 606. The aforementioned stepper motors M1 to M5 may be controlled by a control unit 608 (see FIG. 5).

Figure 6:
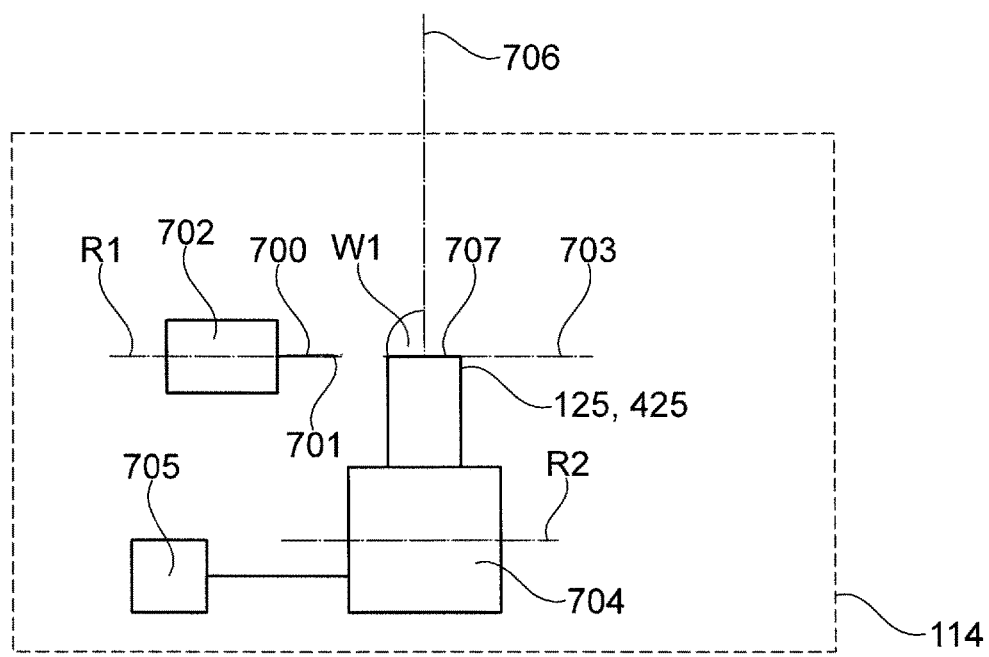
FIG. 6 shows a schematic illustration of an illustrative embodiment of an object preparation device in the form of a microtome in a particle beam apparatus.

FIG. 6 shows a schematic side view of an illustrative embodiment of the object preparation device in the form of the microtome 114, which is arranged in the specimen chamber 120 of the SEM 100, the specimen chamber 201 of the combination apparatus 200 or in the specimen chamber 426 of the particle beam apparatus 400. Therefore, the microtome 114 may be an "in situ microtome".

The microtome 114 may have a cutting device 700 in the form of a knife. By way of example, the cutting device 700 is formed from stainless steel, from diamond and/or from sapphire. However, the system described herein is not restricted to the aforementioned materials. Rather, any material that is usable in the object preparation device in the form of the microtome 114 can be used for the cutting device 700. The cutting device 700 may have a cutting bevel 701 which, for example, has a planoconcave and/or wedge-shaped embodiment. However, the system described herein is not restricted to the aforementioned shapes of the cutting bevel 701. Rather, any form of the cutting bevel 701 that is suitable for the system described herein can be used. A first adjustment unit in the form of a cutting device drive 702 for moving the cutting bevel 701 may be arranged at the cutting device 700. The cutting device drive 702 moves the cutting bevel 701 along a cutting plane 703, in which the cutting bevel 701 may be arranged. By way of example, the cutting plane 703 may be provided by that plane in which the cutting bevel 701 moves in a linear fashion. The cutting bevel 701 may be moved in a substantially linear fashion in an alternative embodiment. In this alternative embodiment, the cutting bevel 701 is arranged at a long lever arm, for example, said lever arm being rotated about a lever arm axis. The cutting bevel 701 may be moved along a circular trajectory on account of the long lever arm. However, this movement may be substantially linear between two positions on the circular trajectory that may be arranged very close together, for example at a distance of a few μm, in particular at a distance of less than 100 μm. Consequently, both the linear movement and the substantially linear movement of the cutting bevel may be performed in the cutting plane 703.

There may be a movement of the cutting bevel 701 relative to the object 125, 425 in the cutting plane 703. In order to expose an area of the object 125, 425, the cutting bevel 701 may be moved relative to the object 125, 425 along the cutting plane 703. Additionally, or as an alternative thereto, provision is made for the object 125, 425 to be moved. By way of example, this is effectuated by a movement by means of the specimen stage 122, 424.

The cutting device 700 and consequently also the cutting bevel 701 may be rotatably mounted about a first rotation axis in the form of an axis of rotation R1. By way of example, the first rotation axis in the form of the axis of rotation R1 is aligned substantially perpendicular to the cutting bevel 701 such that, in the case of a rotation of the cutting device 700 about the first rotation axis in the form of the axis of rotation R1, the cutting bevel 701 intersects the plane of the drawing in FIG. 6 at different angles. By way of example, the first rotation axis in the form of the axis of rotation R1 is aligned parallel to the movement direction along which the cutting device 700 and the object receptacle device 704 are displaceable relative to one another for the purposes of making a cut.

By way of example, the cutting device drive 702 is embodied as a piezo-actuator which moves the cutting bevel 701 in an oscillating fashion. Further, both the cutting speed of the cutting bevel 701, by setting a cutting frequency, and the amplitude of the cutting movement of the cutting device 700 are adjustable in the illustrated illustrative embodiment. Consequently, an oscillating cutting movement of the cutting bevel 701 that is particularly expedient for removing a layer of the object 125, 425 is provided. The oscillating cutting movement of the cutting bevel 701 may be effectuated in the direction of the cutting bevel 701. Expressed differently, the oscillating cutting movement of the cutting bevel 701 may be effectuated along the cutting bevel 701. In principle, the oscillating cutting movement of the cutting bevel 701 corresponds to a back-and-forth movement as in the case of sawing. By contrast, the movement between the cutting bevel 701 and the object 125, 425 for the purposes of making the cut—i.e. for removing a layer from the object 125, 425—may be effectuated substantially perpendicular to the cutting bevel 701 and/or substantially perpendicular to the oscillating cutting movement. Expressed differently, the movement between the cutting bevel 701 and the object 125, 425 for making the cut may be effectuated parallel to the first rotation axis in the form of the axis of rotation R1.

The microtome 114 may have an object receptacle device 704 that may have a movable embodiment. The object 125, 425 may be arranged at the object receptacle device 704. A device axis 706 extends through the object preparation device 114. The device axis 706 may be aligned perpendicular to a surface 707 of the object 125, 425. A second adjustment unit in the form of a stepper motor 705 may be provided for moving the object receptacle device 704. This is discussed in more detail further below.

The cutting plane 703 includes an angle W1 with the device axis 706. The angle W1 may be different from 0°. Accordingly, the device axis 706 does not lie in the cutting plane 703 or it is not arranged parallel to the first plane 703. Moreover, the angle W1 may be less than or equal to 90°. By way of example, the angle W1 lies in the range from 20° to 90° or 30° to 45°, always including the range boundaries. In the illustrative embodiment illustrated in FIG. 6, the angle W1 is 90°.

In the illustrative embodiment of the object preparation device in the form of the microtome 114 illustrated in FIG. 6, the cutting device drive 702 also serves to rotate the cutting bevel 701 about the first rotation axis in the form of the axis of rotation R1. By way of example, the cutting bevel 701 is rotated in a certain angle of rotation out of the plane of the drawing about the first rotation axis in the form of the axis of rotation R1. The angle of rotation may be selected in such a way that the cutting plane 703 and hence the area of the object 125, 425 that is exposed during the cutting process is/are aligned perpendicular or substantially perpendicular to an optical axis of the particle beam apparatus 100, 300, 400. This ensures good imaging and analysis of the exposed area using the particle beam. This is explained in more detail below on the basis of the further figures.

As already explained above, the object receptacle device 704 may have a movable embodiment in the illustrative embodiment of the object preparation device in the form of the microtome 114 illustrated in FIG. 6. The object receptacle device 704 may be movable relative to the further structural units of the microtome 114, to be precise by way of a rotation about a second rotation axis R2 (i.e. an object receptacle rotation axis). The object receptacle device 704 may be rotated about the second rotation axis R2 by means of a second adjustment unit in the form of the stepper motor

705. The first rotation axis in the form of the axis of rotation R1 and the second rotation axis R2 may be aligned parallel to one another. As a result of a rotation of the object receptacle device 704 about the second rotation axis R2, it is possible to align the object 125, 425 in such a way that the surface 707 may be aligned perpendicular or substantially perpendicular to an optical axis of the particle beam apparatus 100, 300 or 400. After rotating the object receptacle device 704 and aligning the surface 707 in respect to the optical axis, the layers of the object 125, 425 may be ablated by means of the cutting bevel 701. This is advantageous in the case of column-shaped embodied objects 125, 425, in particular, said objects having an object axis that extends through the center of the object 125, 425, for example. By moving the object receptacle device 704, it is possible to ablate layers of the object 125, 425 uniformly along the object axis in such a way that layers are ablated along the entire object axis and the object 125, 425 can consequently be examined completely and uniformly. In particular, it is possible to create a 3D reconstruction of the object 125, 425 along the entire object axis by repeated exposure of an area by cutting material off the object 125, 425 and by imaging the exposed area.

Figure 7:
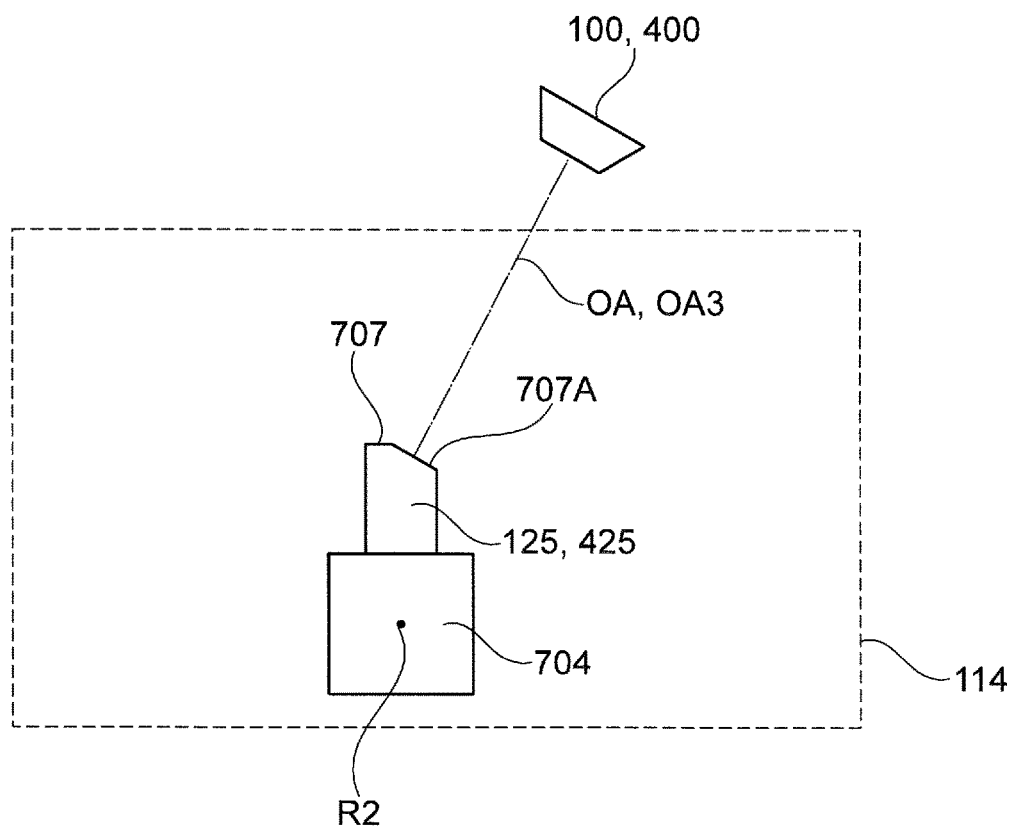
FIG. 7 shows a schematic illustration of an illustrative embodiment of an object preparation device in the form of a microtome in a particle beam apparatus according to FIG. 1 or according to FIG. 3.

FIG. 7 shows a schematic side view of an illustrative embodiment of the object preparation device in the form of the microtome 114, which is arranged in the specimen chamber 120 of the SEM 100 or in the specimen chamber 426 of the particle beam apparatus 400. The microtome 114 of FIG. 7 is based on the microtome 114 of FIG. 6. FIG. 7 shows a view that is rotated by 90° in relation to FIG. 6. The same components are therefore provided with the same reference sign. Reference is made to the explanations provided above, which also apply in this case. FIG. 7 shows the state after the cutting bevel 701 was rotated through a predeterminable angle of rotation, wherein the angle of rotation lies in the range of 5° to 50° or in the range of 10° to 45°, for example, with the range limits being included in the aforementioned ranges. The cutting bevel 701 may be arranged parallel to a surface in the form of a cut surface 707A of the object 125, 425 and moves into the plane of the drawing or out of the plane of the drawing. An area may be exposed by the cutting process with the cutting bevel 701, for example the cut surface 707A illustrated in FIG. 7. The optical axis OA of the SEM 100 or the third optical axis OA3 of the particle beam apparatus 400 may be aligned perpendicular to this exposed cut surface 707A.

Figure 8:
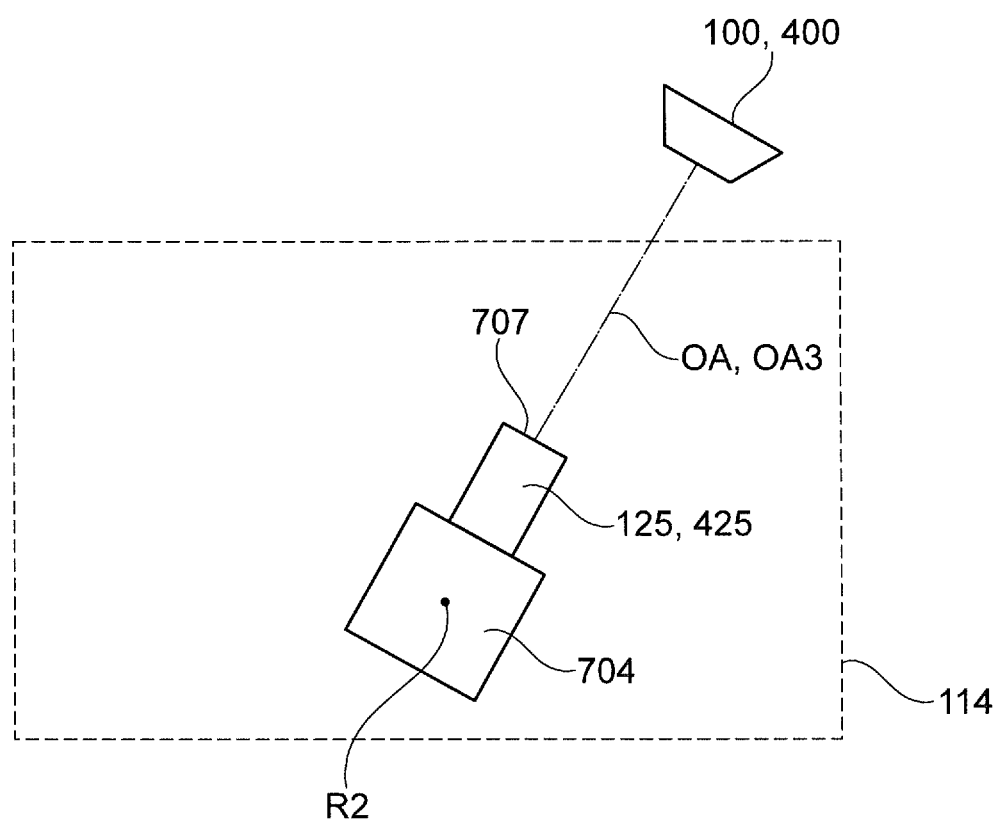
FIG. 8 shows a schematic illustration of a further illustrative embodiment of an object preparation device in the form of a microtome in a particle beam apparatus according to FIG. 1 or according to FIG. 3.

FIG. 8 shows a further schematic side view of the object preparation device in the form of the microtome 114— according to an illustrative embodiment of the invention, which may be arranged in the specimen chamber 120 of the SEM 100 or in the specimen chamber 426 of the particle beam apparatus 400. The microtome 114 of FIG. 8 is based on the microtome 114 of FIGS. 6 and 7. FIG. 8 shows a view that is rotated by 90° in relation to FIG. 6. The same components are therefore provided with the same reference sign. Reference is made to the explanations provided above, which also apply in this case. FIG. 8 shows the state after the cutting bevel 701 was rotated through a predeterminable angle of rotation, wherein the angle of rotation lies in the range of 5° to 50° or in the range of 10° to 45°, for example, with the range limits being included in the aforementioned ranges. In contrast to FIG. 7, the object receptacle device 704 may be additionally rotated about the second rotation axis R2 in the illustrative embodiment illustrated in FIG. 8, to be precise by the identical angle of rotation as the cutting bevel 701. As a result of the rotation of the object receptacle device 704 about the second rotation axis R2, it may be possible to align the object 125, 425 in such a way that the surface 707 of the object 125, 425 may be aligned perpendicular or substantially perpendicular to the optical axis OA of the SEM 100 or perpendicular to the third optical axis OA3 of the particle beam apparatus 400. The cutting bevel 701 may be arranged parallel to the surface 707 and moves into the plane of the drawing or out of the plane of the drawing. An area may be exposed by the cutting process with the cutting bevel 701, for example the surface 707 illustrated in FIG. 8. The optical axis OA of the SEM 100 or the third optical axis OA3 of the particle beam apparatus 400 may be aligned perpendicular to this exposed surface 707.

Figure 9:
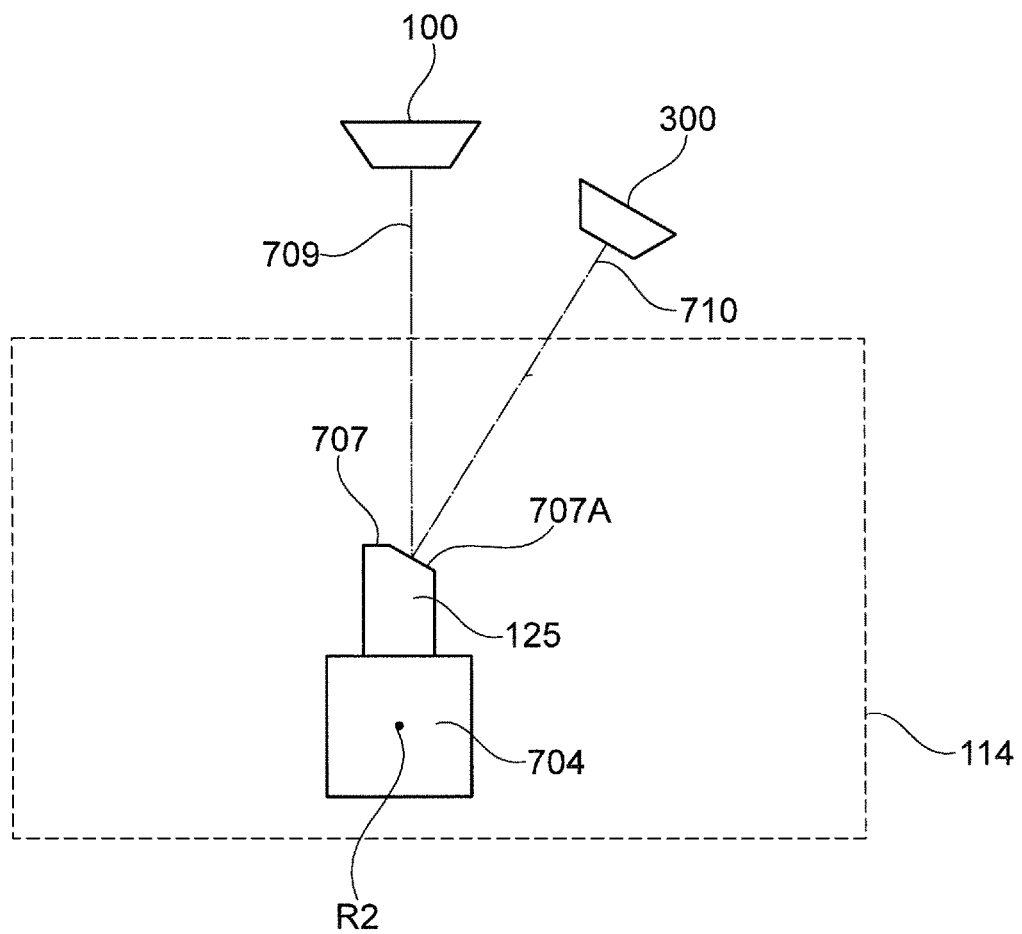
FIG. 9 shows a schematic illustration of an illustrative embodiment of an object preparation device in the form of a microtome in a particle beam apparatus according to FIG. 2.

FIG. 9 shows a schematic side view of an illustrative embodiment of the object preparation device in the form of the microtome 114, which is arranged in the specimen chamber 201 of the combination apparatus 200. The microtome 114 of FIG. 9 is based on the microtome 114 of FIG. 6. FIG. 9 shows a view that is rotated by 90° in relation to FIG. 6. The same components are therefore provided with the same reference sign. Reference is made to the explanations provided above, which also apply in this case. FIG. 9 shows the state after the cutting bevel 701 was rotated through a predeterminable angle of rotation, wherein the angle of rotation lies in the range of 5° to 50° or in the range of 10° to 45°, for example, with the range limits being included in the aforementioned ranges. The cutting bevel 701 may be arranged parallel to a cut surface 707A of the object 125 and moves into the plane of the drawing or out of the plane of the drawing. An area may be exposed by the cutting process with the cutting bevel 701, for example the cut surface 707A illustrated in FIG. 9. The second beam axis 710 of the ion beam apparatus 300 may be aligned perpendicular to this exposed cut surface 707A. The first beam axis 709 of the SEM 100 may be aligned in such a way that the cut surface 707A can be examined and/or imaged.

Figure 10:
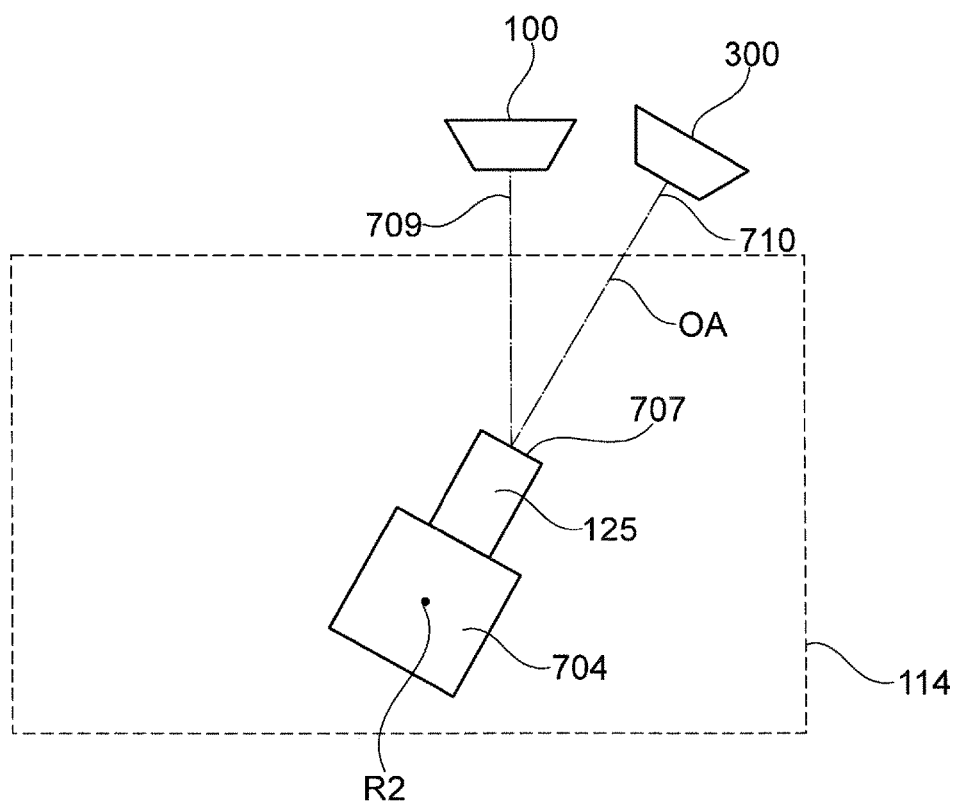
FIG. 10 shows a schematic illustration of a further illustrative embodiment of an object preparation device in the form of a microtome in a particle beam apparatus according to FIG. 2.

FIG. 10 shows a schematic side view of an illustrative embodiment of the object preparation device in the form of the microtome 114, which is arranged in the specimen chamber 201 of the combination apparatus 200. The microtome 114 of FIG. 10 is based on the microtome 114 of FIGS. 6 and 9. FIG. 10 shows a view that is rotated by 90° in relation to FIG. 6. The same components are therefore provided with the same reference sign. Reference is made to the explanations provided above, which also apply in this case. FIG. 10 shows the state after the cutting bevel 701 was rotated through a predeterminable angle of rotation, wherein the angle of rotation lies in the range of 5° to 50° or in the range of 10° to 45°, for example, with the range limits being included in the aforementioned ranges. In contrast to FIG. 9, additionally, the object receptacle device 704 may be rotated about the second rotation axis R2 in the illustrative embodiment illustrated in FIG. 10, to be precise by the identical angle of rotation as the cutting bevel 701. As a result of the rotation of the object receptacle device 704 about the second rotation axis R2, it may be possible to align the object 125 in such a way that the surface 707 of the object 125 may be aligned perpendicular or substantially perpendicular to the second beam axis 710 of the ion beam apparatus 300. The cutting bevel 701 may be arranged parallel to the surface 707 and moves into the plane of the drawing or out of the plane of the drawing. An area may be exposed by the cutting process with the cutting bevel 701, for example the surface 707 illustrated in FIG. 10. The second beam axis 710 of the ion beam apparatus 300 may be aligned perpendicular to this exposed surface 707. The first beam axis 709 of the SEM 100 may be aligned in such a way that the surface 707 can be examined and/or imaged.

Figure 11:
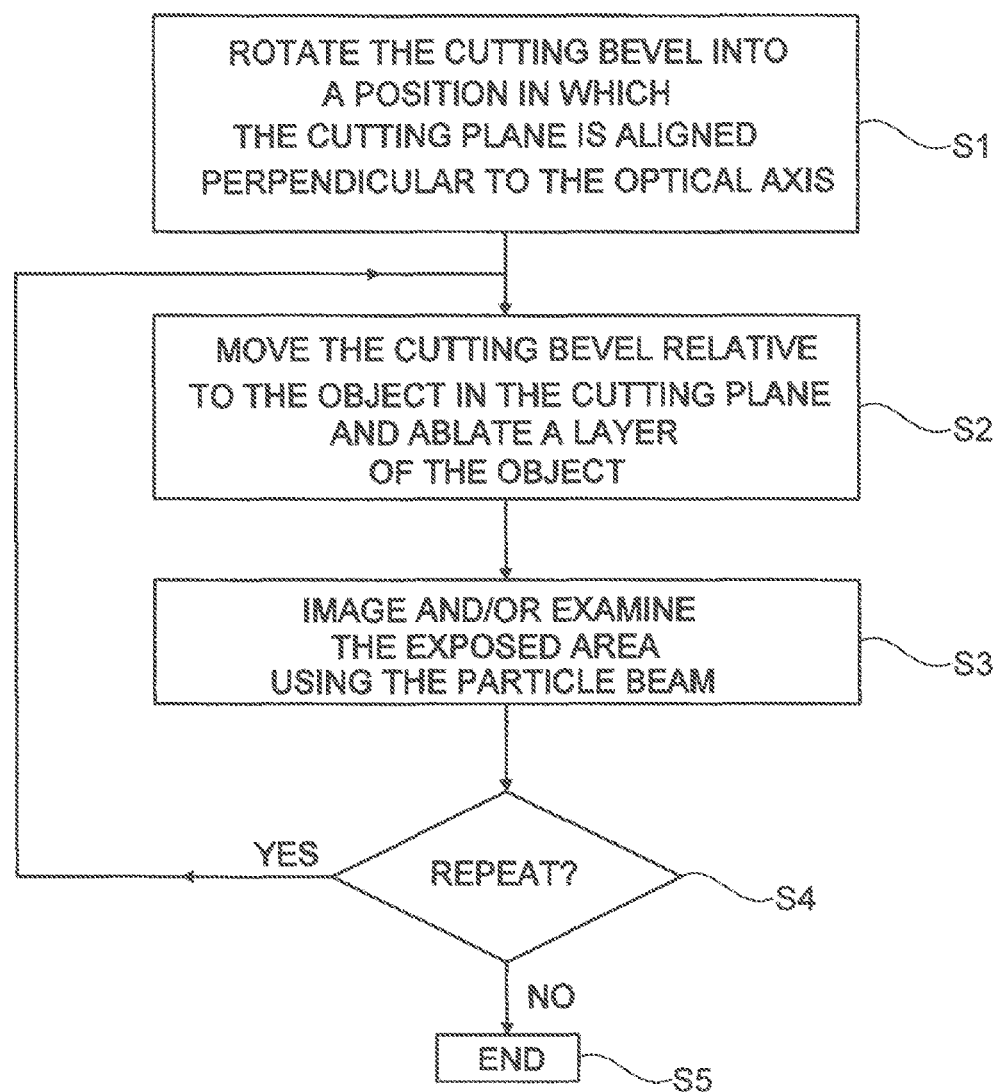
FIG. 11 shows a first illustrative embodiment of a method for operating a particle beam apparatus.

FIG. 11 shows an illustrative embodiment of a method according to the system described herein for operating the particle beam apparatus in the form of the SEM 100, of the combination apparatus 200 or of the particle beam apparatus 400, wherein the particle beam apparatus 100, 200 or 400 has the above-described object preparation device in the form of the microtome 114. The method is explained in an illustrative fashion below on the basis of the operation of the SEM 100. Corresponding statements apply in respect of the methods for operating the further particle beam apparatuses 200 and 400.

In a first method step S1, the cutting bevel 701 may be rotated about the first rotation axis in the form of the axis of rotation R1 in such a way that the cutting plane 703 may be aligned perpendicular or substantially perpendicular to the optical axis OA. In a further method step S2, a movement of the cutting bevel 701 relative to the object 125 in the cutting plane 703 may be brought about. As already mentioned above, the relative movement between the cutting bevel 701 relative to the object 125 parallel to the first rotation axis in the form of the axis of rotation R1 may be carried out in linear or substantially linear fashion. Here, the cutting device 700 can be moved relative to the object receptacle device 704 in the direction of the first rotation axis in the form of the axis of rotation R1 or the object receptacle device 704 can be moved relative to the cutting device 700 parallel to (or in the direction of) the first rotation axis in the form of the axis of rotation R1. A combination of both movements is also possible. A layer of the object 125 may be ablated and an area may be exposed. On account of the alignment of the cutting plane 703, the exposed area of the object 125 may be likewise aligned perpendicular or substantially perpendicular to the optical axis OA. Imaging and/or an examination of the exposed area using the particle beam of the SEM 100, i.e. using the primary electron beam, is/are then carried out in the method step S3. The primary electron beam of the SEM 100 may be guided to the exposed area and interacts with the exposed area. The interaction particles and/or the interaction radiation arises/arise during the interaction. The interaction particles and/or the interaction radiation may be detected by means of at least one of the detectors 116, 117, 119, 121 and 500.

Then, detection signals may be generated by at least one of the detectors 116, 117, 119, 121 and 500. In particular, an image of the exposed area may be generated, said image being stored in a memory (not illustrated here), for example. In the method step S4, there may be a query as to whether the method steps S2 and S3 should be repeated again. If method steps S2 and S3 are intended to be repeated, the object 125 can be moved by means of the object receptacle device 704, for example, in the direction of the cutting bevel 701 in such a way that a further layer can be removed from the object 125 by means of the cutting bevel 701. Following this, method steps S2 and S3 may be repeated. If carrying out the method steps S2 and S3 again is not desired in method step S4, the method according to the system described herein may be stopped (method step S5).

As explained, the aforementioned method steps S2 and S3 can be repeated multiple times in succession in order, repeatedly, to expose areas anew, which are then examined and imaged using the primary electron beam of the SEM 100. In this way, one image may be generated in each case of each exposed area. The generated images can be used to create a 3D reconstruction of the object 125.

Figure 12:
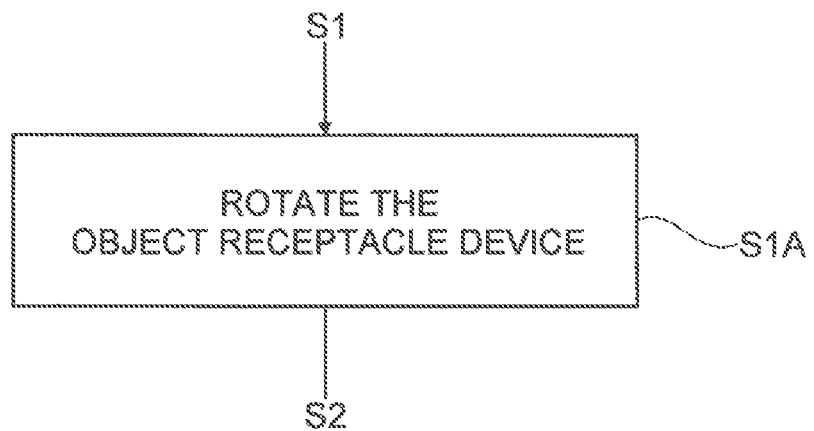
FIG. 12 shows an additional method step for the method according to FIG. 11.

FIG. 12 illustrates a further method step which may be carried out between method step S1 and method step S2, according to an illustrative embodiment of the invention, specifically method step S1A. In a method step S1A, there may be a rotation about the second rotation axis R2 of the object receptacle device 704 relative to the further units of the object preparation device in the form of the microtome 114. As a result of the rotation of the object receptacle device 704 about the second rotation axis R2, it may be possible to align the object 125 in such a way that the surface 707 may be aligned perpendicular or substantially perpendicular to the optical axis OA of the SEM 100.

Figure 13:
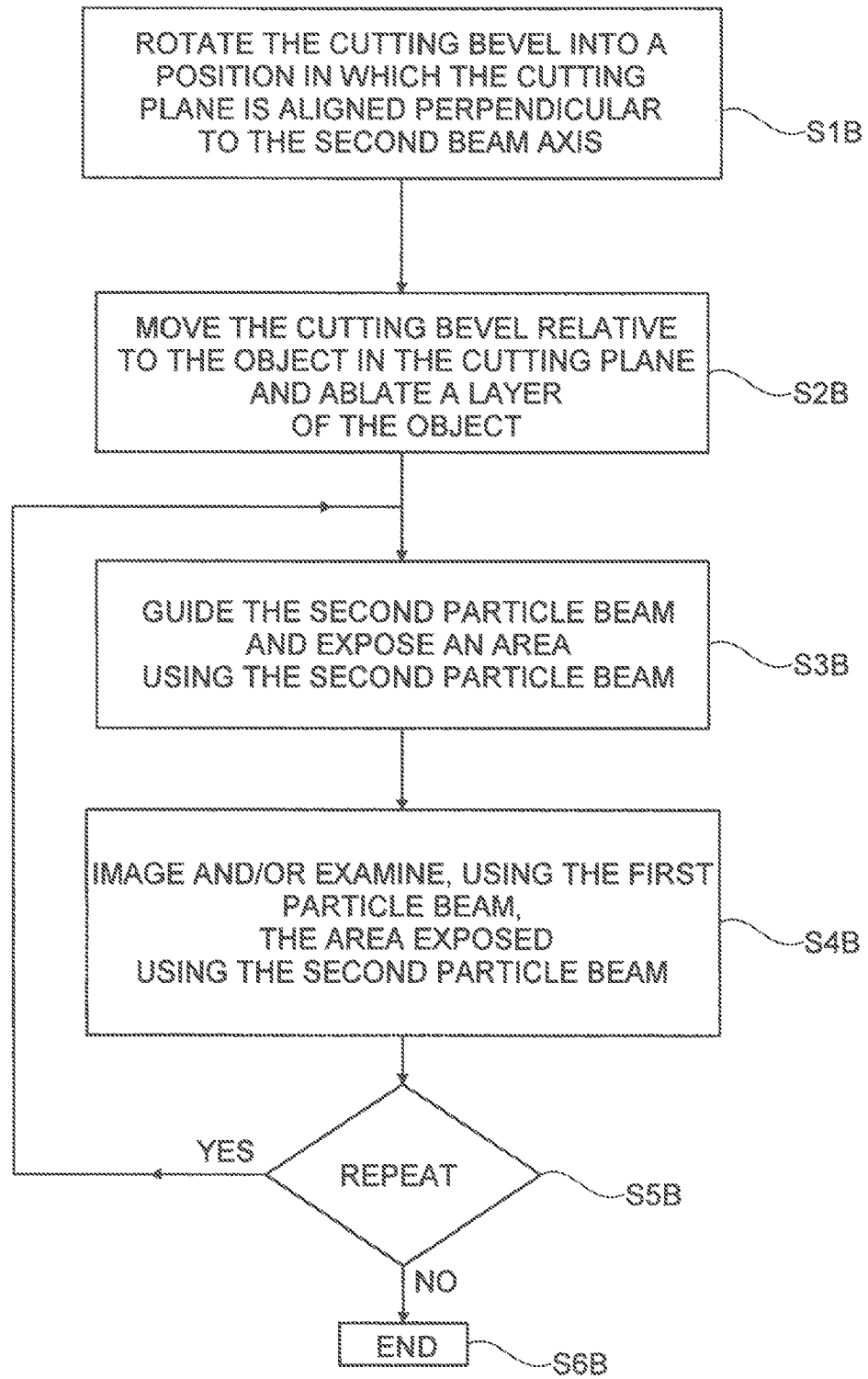
FIG. 13 shows a second illustrative embodiment of a method for operating a particle beam apparatus.

FIG. 13 shows an illustrative embodiment of a method according to the system described herein for operating the particle beam apparatus in the form of the combination apparatus 200, wherein the combination apparatus 200 has the above-described object preparation device in the form of the microtome 114.

In a first method step S1B, the cutting bevel 701 may be rotated about the first rotation axis in the form of the axis of rotation R1 in such a way that the cutting plane 703 is aligned perpendicular or substantially perpendicular to the second beam axis 710 of the ion beam apparatus 300. In a further method step S2B, a movement of the cutting bevel 701 relative to the object 125 in the cutting plane 703 may be brought about. As already mentioned above, the relative movement between the cutting bevel 701 relative to the object 125 parallel to the first rotation axis in the form of the axis of rotation R1 may be carried out in linear or substantially linear fashion. Here, the cutting device 700 can be moved relative to the object receptacle device 704 in the direction of the first rotation axis in the form of the axis of rotation R1 or the object receptacle device 704 can be moved relative to the cutting device 700 parallel to (or in the direction of) the first rotation axis in the form of the axis of rotation R1. A combination of both movements is also possible. A layer of the object 125 may be ablated and an area may be exposed. On account of the alignment of the cutting plane 703, the exposed area of the object 125 may be likewise aligned perpendicular or substantially perpendicular to the second beam axis 710.

Now, in method step S3B, the second particle beam in the form of the ion beam may be guided to the area that was exposed by means of the cutting bevel 701. The second particle beam may be incident on the area exposed by the cutting bevel 701 in a perpendicular or substantially perpendicular manner. Now, by means of the second particle beam, material of the object 125 may be ablated perpendicular to the area exposed by means of the cutting bevel 701. As a result of this, an area of the object 125 may be exposed in turn, i.e. an area exposed by the second particle beam.

Then, imaging and/or an examination of the area exposed by the second particle beam may be carried out in the method step S4B using the first particle beam in the form of the primary electron beam of the SEM 100. The primary electron beam of the SEM 100 may be guided to the area exposed by the second particle beam and interacts with this exposed area. The interaction particles and/or the interaction radiation arises/arise during the interaction. The interaction particles and/or the interaction radiation may be detected by means of at least one of the detectors 116, 117, 119, 121 and 500.

Then, detection signals may be generated by at least one of the detectors 116, 117, 119, 121 and 500. In particular, an image of the area exposed by the second particle beam may be generated, said image being stored in a memory (not illustrated here), for example. In the method step S5B, there may be a query as to whether the method steps S3B and S4B should be repeated again. Method steps S3B and S4B may be repeated in the affirmative. Yet another area may be exposed by the second particle beam. Subsequently, this yet another area may be examined and/or imaged using the first particle beam. If carrying out the method steps S3B and S4B again is not desired in method step S5B, the method according to the system described herein may be stopped (method step S6B).

As explained, the aforementioned method steps S3B and S4B can be repeated multiple times in succession in order, repeatedly, to expose areas anew, which are then examined and imaged using the primary electron beam of the SEM 100. In this way, one image may be generated in each case of each exposed area. The generated images can be used to create a 3D reconstruction of the object 125.

The imaging and/or the examination in method step S4B can also be carried out, alternatively or additionally, using the second particle beam in the form of the ion beam.

The features of the system described herein disclosed in the present description, in the drawings and in the claims may be essential for the realization of the system described herein in the various embodiments thereof, both individually and in arbitrary combinations. The system described herein is not restricted to the described embodiments herein, and may be varied within the scope of the claims, taking into account the knowledge of the relevant person skilled in the art. Other embodiments of the system described herein will be apparent to those skilled in the art from a consideration of the specification and/or an attempt to put into practice the invention disclosed herein. It is intended that the specification and examples be considered as illustrative only, with the true scope and spirit of the invention being indicated by the following claims.

The invention claimed is:

1. A particle beam apparatus for analyzing and/or for processing an object, comprising:
   at least one beam generator for generating a particle beam comprising charged primary particles;
   an optical axis;
   at least one objective lens for focusing the particle beam onto the object, wherein interaction particles and/or interaction radiation arise/arises during an interaction of the particle beam with the object;
   at least one detector for detecting the interaction particles and/or the interaction radiation; and
   at least one object preparation device for preparing an object in the particle beam apparatus, the at least one object preparation device having:
      at least one object receptacle device for receiving the object,
      at least one cutting device, and
      at least one cutting bevel for cutting the object, wherein the cutting bevel is arranged at the cutting device,
   wherein:
      the cutting bevel lies in a cutting plane,
      an axis of rotation lies in the cutting plane, and
      the cutting bevel is embodied to be rotatable about the axis of rotation in such a way that the cutting plane is aligned perpendicular or substantially perpendicular to the optical axis of the particle beam apparatus.

2. The particle beam apparatus according to claim 1, wherein the at least one cutting bevel and the at least one object receptacle device are movable in a linear fashion relative to one another in a direction of the axis of rotation.

3. The particle beam apparatus according to claim 1, wherein the at least one object receptacle device is embodied to be movable.

4. The particle beam apparatus according to claim 1, wherein the at least one object preparation device has at least one of the following features:
   at least one first adjustment unit for rotating the cutting bevel about the axis of rotation;
   at least one second adjustment unit for rotating the at least one object receptacle device about an object receptacle rotation axis.

5. The particle beam apparatus according to claim 1, wherein the at least one object preparation device is mountable on a movably embodied object stage of the particle beam apparatus.

6. The particle beam apparatus according to claim 1, wherein the axis of rotation is aligned perpendicular or substantially perpendicular to the cutting bevel.

7. The particle beam apparatus according to claim 1, wherein the particle beam apparatus has at least one of the following features:
   the at least one object preparation device is arranged at a movably embodied object stage of the particle beam apparatus, wherein the object stage is embodied to be movable along a first stage axis, a second stage axis and a third stage axis, wherein the first stage axis, the second stage axis and the third stage axis are aligned perpendicular to one another; and
   the at least one object preparation device is arranged at a movably embodied object stage of the particle beam apparatus, wherein the object stage is embodied to be movable along a first stage axis, a second stage axis and a third stage axis, wherein the first stage axis, the second stage axis and the third stage axis are aligned perpendicular to one another, wherein the object stage is embodied to be rotatable about a first stage rotation axis and/or about a second stage rotation axis, wherein the first stage rotation axis is aligned perpendicular to the second stage rotation axis.

8. The particle beam apparatus according to claim 1, wherein the particle beam apparatus has at least one mirror corrector for correcting chromatic and/or spherical aberration.

9. The particle beam apparatus according to claim 1, wherein the particle beam apparatus is designed as an electron beam apparatus and/or as an ion beam apparatus.

10. The particle beam apparatus according to claim 1, wherein the at least one beam generator for generating the particle beam comprising charged primary particles is embodied as a first beam generator for generating a first particle beam comprising first charged primary particles and the at least one objective lens is embodied as a first objective lens for focusing the first particle beam, and wherein the particle beam apparatus further comprises:
   at least one second beam generator for generating a second particle beam comprising second charged primary particles, and
   at least one second objective lens for focusing the second particle beam onto the object.

11. The particle beam apparatus according to claim 10, wherein:
   the first beam generator for generating the first particle beam with first charged primary particles and the first objective lens for focusing the first particle beam are arranged in a first particle beam column, wherein the first particle beam column has a first beam axis,
   the at least one second beam generator for generating the second particle beam with second charged primary particles and the at least second objective lens for focusing the second particle beam are arranged in a second particle beam column, wherein the second particle beam column has a second beam axis, the first beam axis and the second beam axis include a beam axis angle that differs from 0° and 180°, and the cutting plane is aligned perpendicular to the first beam axis in a first position of the cutting device and is aligned perpendicular to the second beam axis in a second position of the cutting device.

12. A method for operating a particle beam apparatus for analyzing and/or for processing an object, the particle beam apparatus having at least one beam generator for generating a particle beam comprising charged primary particles, an optical axis, at least one objective lens for focusing the particle beam onto the object, wherein interaction particles and/or interaction radiation arise/arises during an interaction of the particle beam with the object, at least one detector for detecting the interaction particles and/or the interaction radiation, and at least one object preparation device for preparing an object in the particle beam apparatus, the at least one object preparation device having at least one object receptacle device for receiving the object, at least one cutting device, and at least one cutting bevel for cutting the object, wherein the cutting bevel is arranged at the cutting device, wherein the cutting bevel lies in a cutting plane, an axis of rotation lies in the cutting plane, and the cutting bevel is embodied to be rotatable about the axis of rotation in such a way that the cutting plane is aligned perpendicular or substantially perpendicular to the optical axis of the particle beam apparatus, the method comprising the following steps:

rotating the cutting bevel about the axis of rotation through an angle of rotation into a position in which the cutting plane is aligned perpendicular to the optical axis, and moving the cutting bevel relative to the object in the cutting plane.

13. The method according to claim 12, wherein the at least one object receptacle device is rotated through an object receptacle angle of rotation in such a way that a surface of the object is aligned perpendicular to the optical axis.

\* \* \* \* \*